US010512764B2

United States Patent
Ngo-Chu et al.

(10) Patent No.: US 10,512,764 B2
(45) Date of Patent: Dec. 24, 2019

(54) ACTUATION FEATURES FOR DILATION SYSTEM

(71) Applicant: Acclarent, Inc., Irvine, CA (US)

(72) Inventors: Don Q. Ngo-Chu, Irvine, CA (US); George L. Matlock, Pleasanton, CA (US)

(73) Assignee: Acclarent, Inc., Irvine, CA (US)

( * ) Notice: Subject to any disclaimer, the term of this patent is extended or adjusted under 35 U.S.C. 154(b) by 277 days.

(21) Appl. No.: 15/333,620

(22) Filed: Oct. 25, 2016

(65) Prior Publication Data

US 2018/0110968 A1    Apr. 26, 2018

(51) Int. Cl.
*A61M 29/02*   (2006.01)
*A61M 25/10*   (2013.01)
(Continued)

(52) U.S. Cl.
CPC ............. *A61M 29/02* (2013.01); *A61B 34/00* (2016.02); *A61M 25/0113* (2013.01); *A61M 25/0136* (2013.01); *A61M 25/09041* (2013.01); *A61M 25/10182* (2013.11); *A61B 17/22031* (2013.01); *A61B 17/24* (2013.01); *A61B 2017/00017* (2013.01); *A61B 2017/00022* (2013.01); *A61B 2017/22034* (2013.01);
(Continued)

(58) Field of Classification Search
CPC .............. A61M 29/02; A61M 25/0113; A61M 25/0136; A61M 25/10182; A61M 25/09041; A61B 34/00
See application file for complete search history.

(56) References Cited

U.S. PATENT DOCUMENTS 9,155,492 B2   10/2015   Jenkins et al.
9,554,817 B2   1/2017   Goldfarb et al.
(Continued)

FOREIGN PATENT DOCUMENTS

WO   WO 2016/040820 A1   3/2016

OTHER PUBLICATIONS

International Search Report and Written Opinion dated Feb. 23, 2018 for International Application No. PCT/US2017/055694, 25 pages.
(Continued)

*Primary Examiner* — Richard G Louis
(74) *Attorney, Agent, or Firm* — Frost Brown Todd LLC

(57) ABSTRACT

An apparatus includes a handle, a guide member, a dilation catheter, a guidewire, and first and second movement assemblies. The dilation catheter is slidably housed within the handle and is slidable relative to the guide member. The guidewire is translatable relative to the dilation catheter. The first movement assembly is configured to actuate relative to the handle and includes a first body fixed with the dilation catheter and a first coupling member. The second movement assembly is proximal in relation to the first movement assembly and includes a second body and a second coupling member. The second body is configured to selectively fix to the guidewire and actuate relative to the handle. The first coupling member and the second coupling member are configured to connect the first movement assembly and the second movement assembly to translate together relative to handle in response to distal translation of the first movement assembly.

20 Claims, 28 Drawing Sheets

(51) Int. Cl.
  *A61M 25/01*   (2006.01)
  *A61M 25/09*   (2006.01)
  *A61B 34/00*   (2016.01)
  *A61B 17/24*   (2006.01)
  *A61M 25/06*   (2006.01)
  *A61B 17/22*   (2006.01)
  *A61B 17/00*   (2006.01)
  *A61B 90/00*   (2016.01)

(52) U.S. Cl.
  CPC ............ *A61B 2017/22038* (2013.01); *A61B 2090/065* (2016.02); *A61M 2025/0681* (2013.01); *A61M 2029/025* (2013.01); *A61M 2210/0675* (2013.01); *A61M 2210/0681* (2013.01)

(56) References Cited

U.S. PATENT DOCUMENTS

| | | | |
|---|---|---|---|
| 2002/0111666 A1* | 8/2002 | Hart | A61F 2/95 623/1.11 |
| 2008/0183128 A1 | 7/2008 | Morriss et al. | |
| 2008/0287908 A1* | 11/2008 | Muni | A61B 17/24 604/506 |
| 2010/0030031 A1 | 2/2010 | Goldfarb et al. | |
| 2010/0099946 A1* | 4/2010 | Jenkins | A61B 1/0014 600/104 |
| 2011/0004057 A1 | 1/2011 | Goldfarb et al. | |
| 2013/0116724 A1* | 5/2013 | Clark | A61B 17/0057 606/200 |
| 2014/0074141 A1 | 3/2014 | Johnson et al. | |
| 2015/0057575 A1* | 2/2015 | Tsusaka | A61B 1/0055 600/587 |
| 2015/0119923 A1 | 4/2015 | Liberatore et al. | |
| 2016/0058985 A1 | 3/2016 | Lam et al. | |
| 2016/0082233 A1 | 3/2016 | Ha et al. | |
| 2017/0055818 A1 | 3/2017 | Kermani | |

OTHER PUBLICATIONS

International Preliminary Report on Patentability dated Apr. 30, 2019 for International Application No. PCT/US2017/055694, 14 pages.

* cited by examiner

ACTUATION FEATURES FOR DILATION SYSTEM

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Irvine, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Irvine, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 7I depicts a side schematic view of the instrument of FIG. 7A, where the distal portion of the guide catheter of FIG. 7A is aligned in relation to a targeted ostium of a patient and the guidewire of FIG. 7A has exited the distal portion of the guide catheter and has entered through the ostium;

Figure 1:
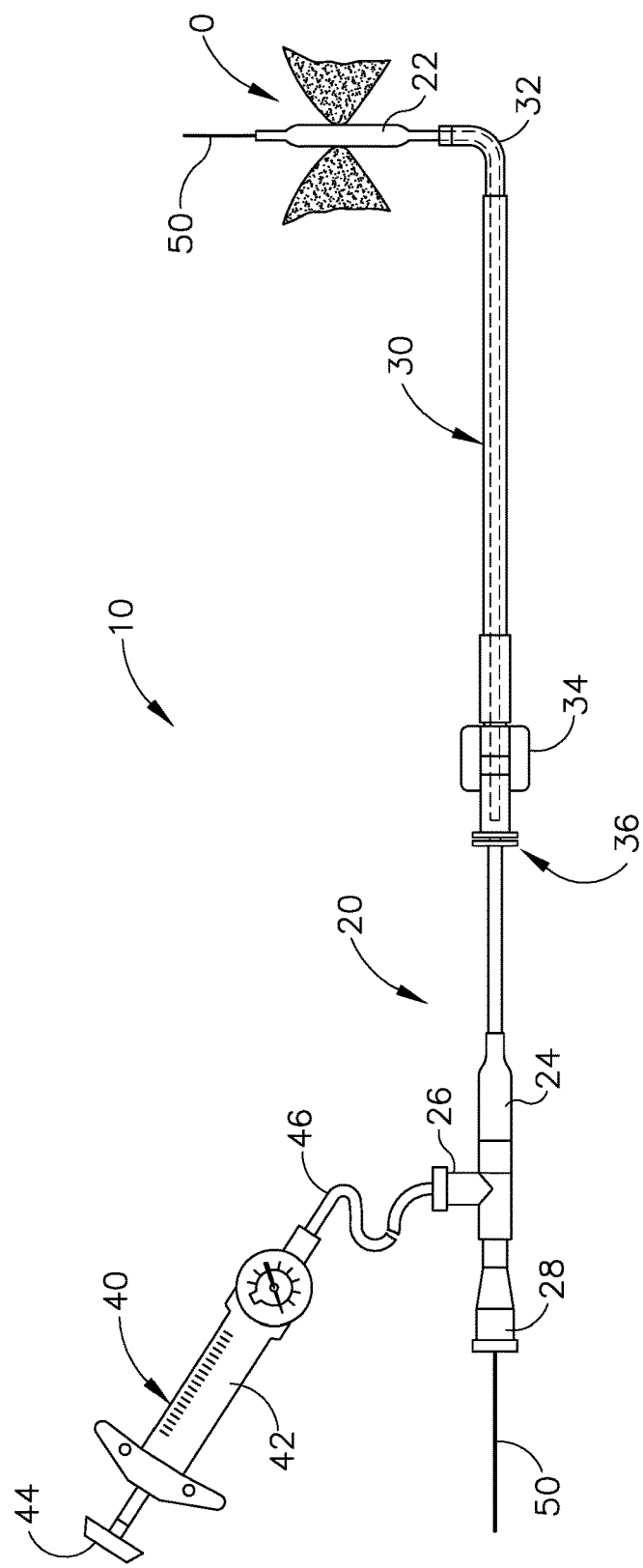
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; the Eustachian tube of the ear; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Irvine, Calif.

The distal end of dilation catheter (20) includes an inflatable dilator (22). The proximal end of dilation catheter (20)

includes a grip (24), which has a lateral port (26) and an open proximal end (28). Dilation catheter (20) includes a first lumen (not shown) that provides fluid communication between lateral port (26) and the interior of dilator (22). Dilator (22) may include any appropriate material, including a polyether block amide such as Pebax®. Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilation catheter (20) is configured similar to the Relieva Ultirra™ Sinus Balloon Catheter by Acclarent, Inc. of Irvine, Calif. In some other versions, dilator catheter (20) is configured similar to the Relieva Solo Pro™ Sinus Balloon Catheter by Acclarent, Inc. of Irvine, Calif. Other suitable forms that dilator catheter (20) may take will be apparent to those of ordinary skill in the art in view of the teachings herein.

Guide catheter (30) of the current example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Irvine, Calif. Other suitable forms that guide catheter (30) may take will be apparent to those of ordinary skill in the art in view of the teachings herein.

Inflator (40) of the current example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the current example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire (50) is configured similar to the Relieva Luma Sentry™ Sinus Illumination System by Acclarent, Inc. of Irvine, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as an ostium. Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium to be dilated. This positioning of guide catheter (30) may be performed under visualization provided by an endoscope. After guide catheter (30) has been positioned, the operator may advance guidewire (50) distally through guide catheter (30) and second lumen (not shown) such that a distal portion of the guidewire (50) passes through the sinus ostium and into the sinus cavity. The operator may illuminate a distal end of guidewire, which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (or some other targeted anatomical passageway). After dilator (22) has been positioned within the ostium, dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium, such as by remodeling the bone, etc., forming ostium. By way of example only, dilator (22) may be inflated to a pressure of about 10 to about 12 atmospheres. Dilator (22) may be held at this volume for a few seconds to sufficiently open the ostium (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

In some instances, it may be desirable to irrigate the paranasal sinus and/or the nasal cavity after dilation catheter (20) has been used to dilate an ostium. Such irrigation may be performed to flush out purulence, etc. that may be present after the dilation procedure. By way of example only, such irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Irvine, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Irvine, Calif. Of course, irrigation may be provided in the absence of a dilation procedure; and a dilation procedure may be completed without also including irrigation.

II. Overview of Exemplary Dilation Catheter Instrument

FIGS. 2-4E show an instrument (100) that may be used to treat a paranasal sinus drainage passageway (e.g., a frontal recess, a frontal sinus ostium, a maxillary sinus ostium, a sphenoid sinus ostium, etc.) or a Eustachian tube passageway. For instance, instrument (100) may be used to dilate a paranasal sinus drainage passageway or a Eustachian tube. The various features of instrument (100) may be readily incorporated into dilation catheter system (10) discussed above. Instrument (100) of this example includes a handle (102), a guide catheter (130) removably coupled with handle (102), a dilation catheter (120) slidably housed within both handle (102) and guide catheter (130), a guidewire (150), a guidewire movement mechanism (160), and a dilation catheter movement assembly (170).

Figure 2:
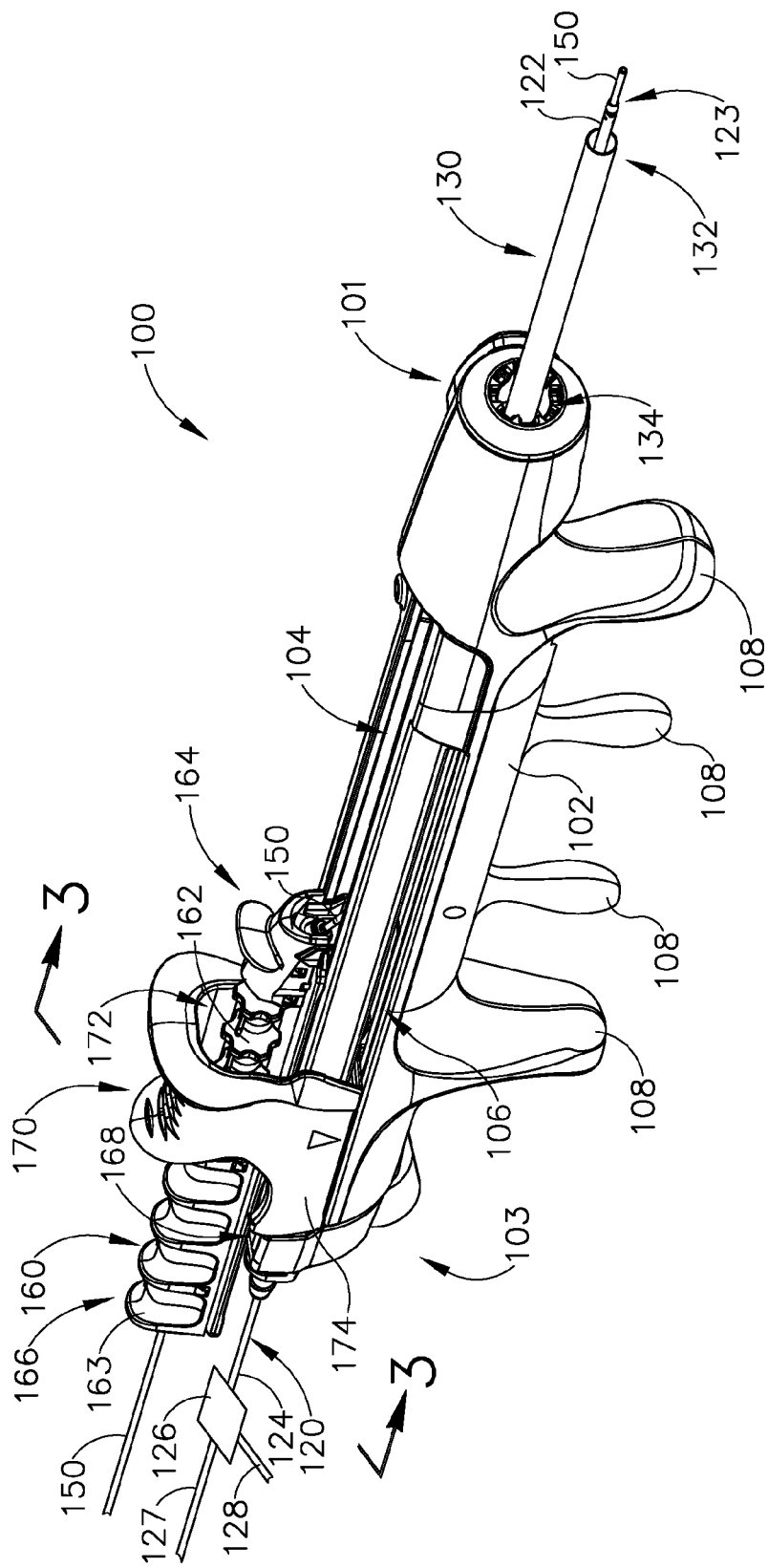
FIG. 2 depicts a perspective view of an instrument suitable for incorporation with the dilation catheter system of FIG. 1.
Figure 3:
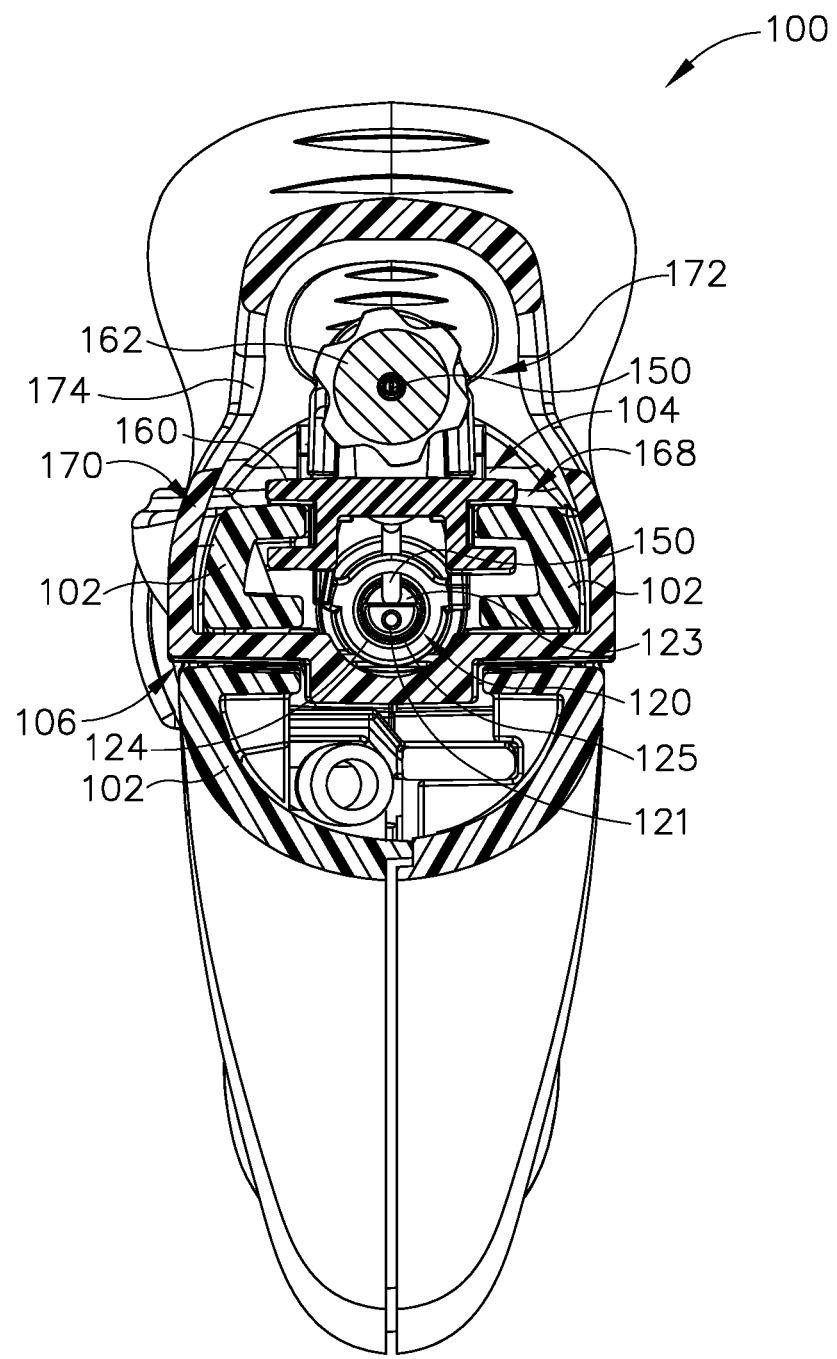
FIG. 3 depicts cross-sectional view of the instrument of FIG. 2, taken along line 3-3 of FIG. 2.

As shown in FIGS. 2-4, handle (102) of the current example extends from a proximal end (103) to a distal coupling assembly (101) defining a longitudinal axis along the length of handle (102). Handle (102) defines a top slot (104) and a pair of side slots (106). As will be described in greater detail below, top slot (104) is dimensioned to slidably house a portion of guidewire movement assembly (160) while side slots are dimensioned to slidably house a portion of dilation catheter movement assembly (170). Additionally, distal coupling assembly (101) is configured to selectively couple with guide catheter (130) such that a plurality of guide catheters (130) may be separately incorporated into instrument (100).

Distal coupling assembly (101) may incorporate any suitable coupling components that would be apparent to one having ordinary skill in the art in view of the teachings herein. In one merely illustrative example, coupling assembly (101) may include a latch resiliently biased within handle (102) to a locked position while a proximal portion (134) of guide catheter (130) may include a notch configured to cam against the latch when guide catheter (130) is inserted into coupling assembly (101). The latch may then snap into the notch in order to effectively lock guide catheter (130) to handle (102). Of course, there may be an external button allowing an operator to force latch to disengage notch such that guide catheter (130) may be removed from coupling assembly (101). Other suitable components and configurations that may be used to form coupling assembly (101) will be apparent to those of ordinary skill in the art in view of the teachings herein.

Handle (102) further includes a fluid port (105) and finger anchoring pegs (108). In the current example, fluid port (105) is configured to couple with a source of suction to provide suction via guide catheter (130). In addition, or in the alternative, fluid port (105) may be coupled with a fluid source to provide irrigation. Other suitable ways in which fluid port (105) may be made and used will be apparent to those of ordinary skill in the art in view of the teachings herein. Handle (102) is sized and shaped such that instrument (100) can be manipulated and operated by a user (such as a physician) in a convenient and efficient single-handed manner if so desired, with finger anchoring pegs (108) promoting gripping of handle (102) with a single hand. Handle (102) can be formed of any suitable material including, for example, polycarbonate and ABS (acetonitrile butadiene styrene) and can be manufactured using any suitable technique including, for example, injection molding of two clamshell handle halves. Various suitable materials and methods that may be used to manufacture handle (102) will be apparent to those of ordinary skill in the art in view of the teachings herein.

In the current example, guide catheter (130) serves as a substitute for guide catheter (30) described above and shown in FIG. 1. Guide catheter (130) of this example is attached to distal coupling assembly (101) of handle (102) and defines an inner lumen (i.e., inner passage). Guide catheter (130) extends along longitudinal axis defined by handle (102) and has a proximal portion (134) and an open distal end (132). As described above, proximal portion (134) is dimensioned to selectively couple with distal coupling assembly (101) of handle (102).

In the current example, open distal end (132) of guide catheter (130) extends along a straight, linear path. However, this is merely optional. Open distal end (132) may have any suitable bend or curve along its longitudinal profile that would be apparent to one having ordinary skill in the art in view of the teachings herein. For example, open distal end (132) may have a longitudinal profile similar to that of bent distal end (32) of guide catheter (30) described above. It should be understood that since guide catheter (130) is capable of selectively coupling with distal coupling assembly (101) of handle (102), an operator may attach a guide catheter having desired dimensions, including longitudinal profile, in order to access a desired location within a patient, such as a specific paranasal sinus ostium or other anatomical passageway. Various suitable dimensions and longitudinal profiles will be apparent to one having ordinary skill in the art in view of the teachings herein.

Dilation catheter (120) serves as a substitute for dilator catheter (20) described above. Dilation catheter (120) includes a dilator (122), a shaft (124), a manifold (126), an inflation port (127), and an irrigation port (128). Inflation port (127) and irrigation port (128) extend from manifold (126). Manifold (126) is connected to the proximal end of shaft (124). Manifold (126) provides fluid communication for selected lumens defined by shaft (124) with inflation port (127) and irrigation port (128), respectively. While in the current example, a manifold (126) is used to act as a junction for shaft (124) with both inflation port (127) and irrigation port (128); any other suitable connections may be used as would be apparent to one having ordinary skill in the art in view of the teachings herein. For example, inflation port (127) and irritation port (128) may proximally extend from their respective lumens defined by shaft (124), effectively eliminating manifold (126).

As best seen in FIG. 3, shaft (124) defines a first lumen (121), a second lumen (123), and a third lumen (125). First lumen (121) extends from inflation port (127), through manifold (126) and shaft (124), and terminates in dilator (122). First lumen (121) provides a path for fluid communication between inflation port (127) and dilator (122). Inflation port (127) may thus be coupled with a fluid source (e.g., inflator (40), etc.) to provide selective inflation of dilator (122) in accordance with the teachings herein. Second lumen (123) of dilation catheter (120) extends from a slot defined by shaft (124) within handle (102) all the way to the open distal end of dilation catheter (120) to provide a passageway to slidably receive guidewire (150) as described below. Third lumen (125) extends from irrigation port (128), through manifold (126) and shaft (124), past dilator (122) and terminates at apertures adjacent to open distal end of dilation catheter (120). Irrigation port (128) may thus be coupled with an irrigation source to provide selective irrigation in accordance with the teachings herein. Dilation catheter (120) is slidably disposed at least partially in handle (102) and in the lumen of guide catheter (130). Dilation catheter (120) may be configured and operable in accordance with any suitable dilation catheters known to one skilled in the art.

Figure 4A:
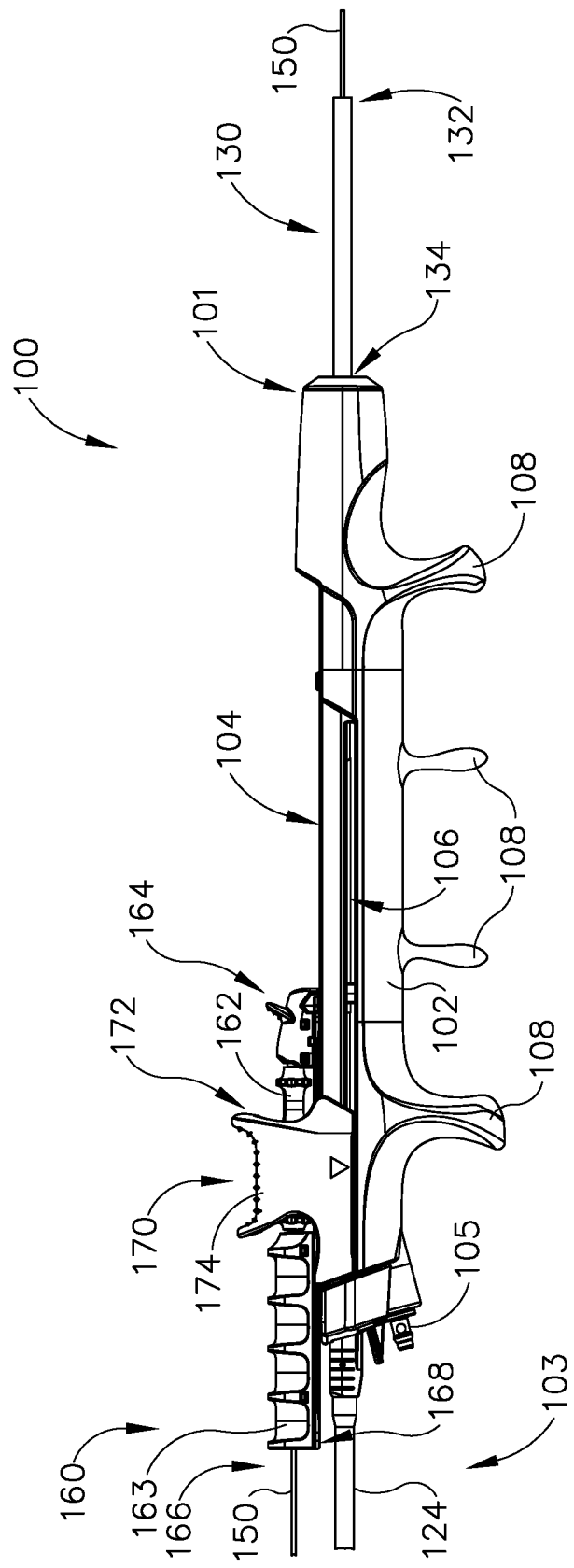
FIG. 4A depicts a side elevational view of the instrument of FIG. 2, with a guidewire and a dilation catheter in a proximal position.
Figure 4B:
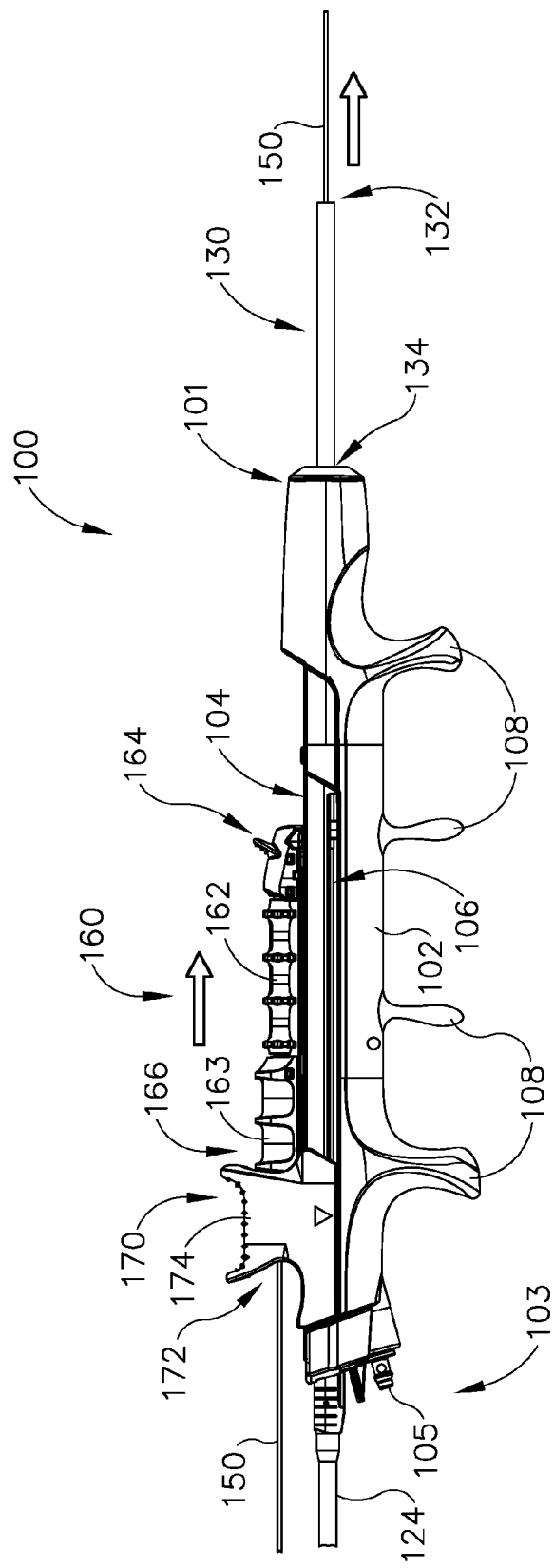
FIG. 4B depicts a side elevational view of the instrument of FIG. 2, with the guidewire of FIG. 4A advanced to a distal position, while the dilation catheter of FIG. 4A remains in the proximal position.
Figure 4C:
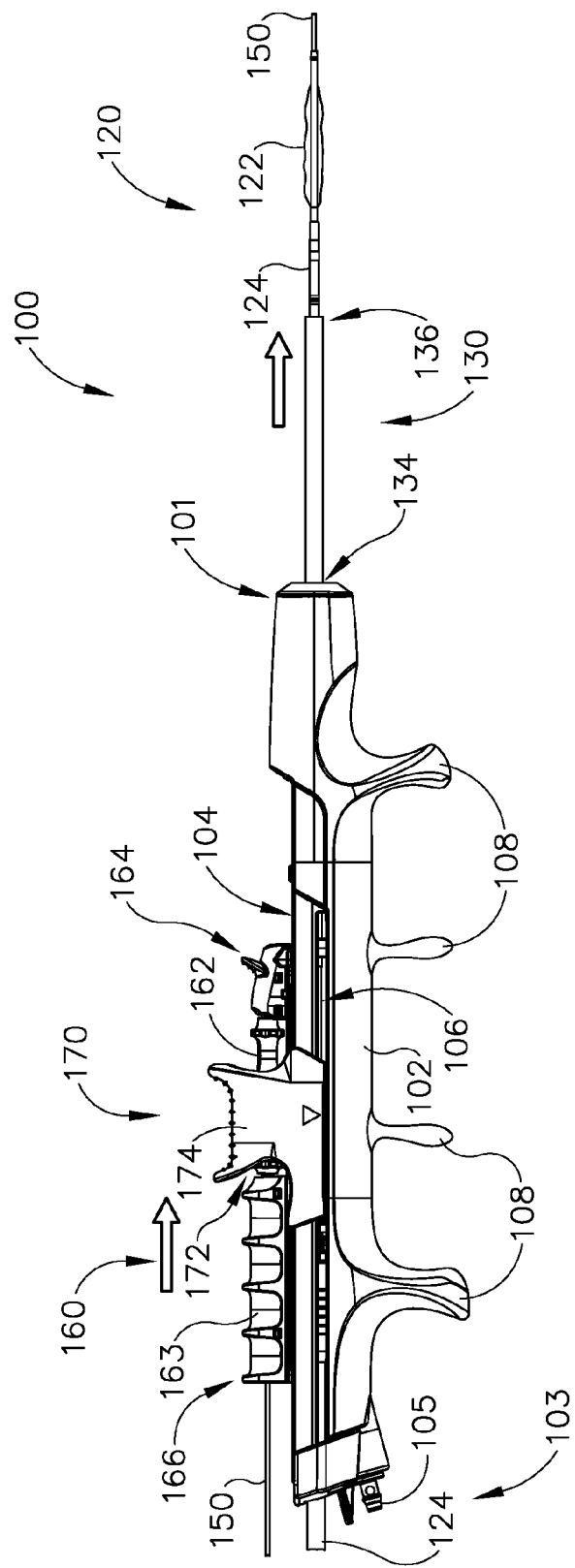
FIG. 4C depicts a side elevational view of the instrument of FIG. 2, with the guidewire and the dilation catheter of FIG. 4A advanced to the distal position, while a dilator is in an unexpanded state.
Figure 4D:
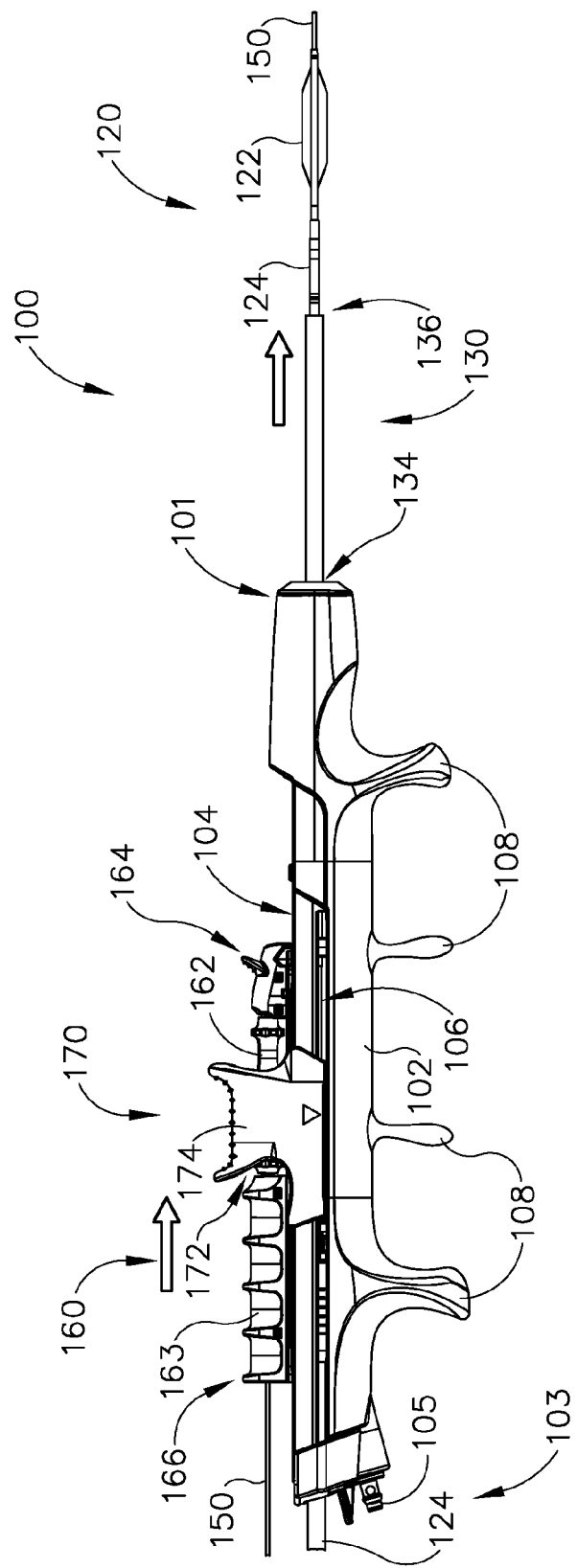
FIG. 4D depicts a side elevational view of the instrument of FIG. 2, with the guidewire and the dilation catheter of FIG. 4A advanced to a distal position, while the dilator of FIG. 4C is in an expanded state.
Figure 4E:
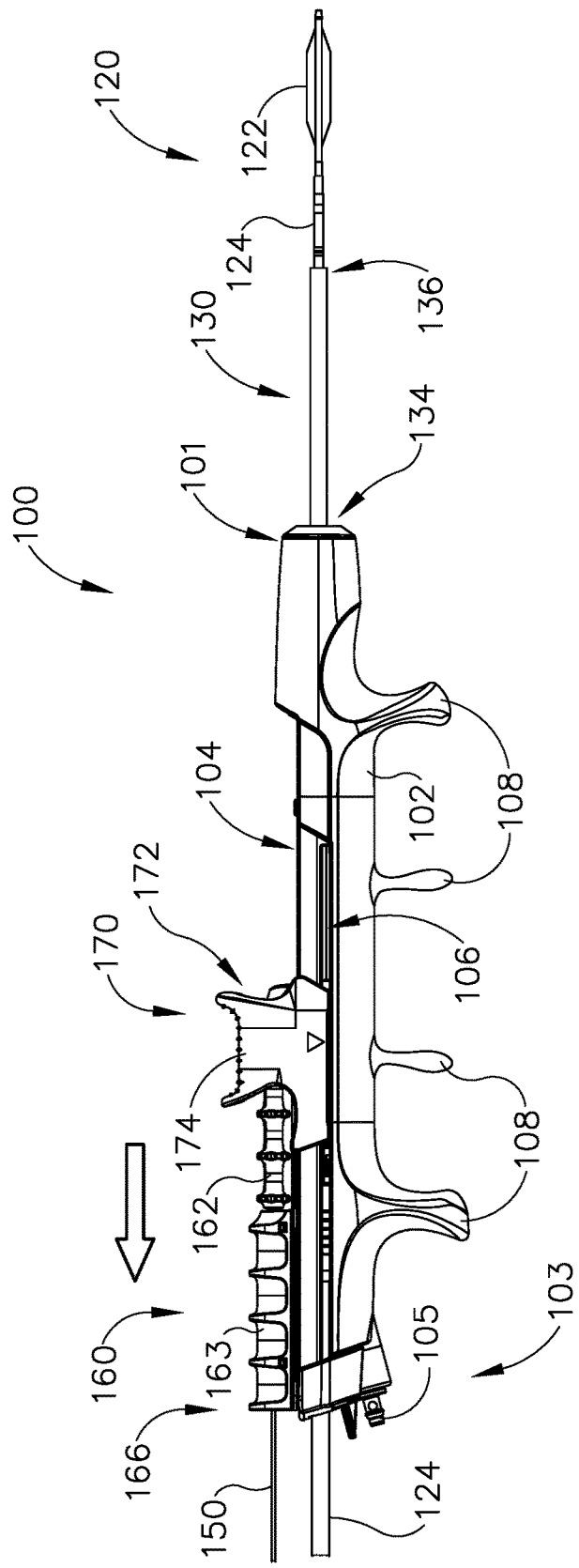
FIG. 4E depicts a side elevational view of the instrument of FIG. 2, with the guidewire of FIG. 4A retracted to the proximal position and the dilation catheter of FIG. 4A in the distal position, while the dilator of FIG. 4C is in an expanded state.

During operation of instrument (100), as will be described in greater detail below, dilation catheter movement assembly (170) may translate dilation catheter (120) between a proximal position and a distal position. In particular, dilation catheter (120) may be longitudinally advanced and retracted relative to handle (102) and through the lumen of guide catheter (130). When dilation catheter (120) is in the proximal position, as shown in FIGS. 4A-4B, dilator (122) may be positioned within the lumen of guide catheter (130), proximal to open distal end (132) of guide catheter (130). When dilation catheter (120) is in the distal position, as shown in FIGS. 4C-4E, dilator (122) may be positioned distal to the distal end (132) of guide catheter (130). Of course any other suitable location of dilator (122) relative to guide catheter (130) corresponding to proximal and distal positions may be used as would be apparent to one having ordinary skill in the art.

Dilation catheter movement assembly (170) includes a body (174) defining a pathway (172). Body (174) extends into side slots (106) of handle (102) in order to slidably couple with handle (102). Body (174) is also fixed to shaft (124) of dilation catheter (120). Therefore, dilation catheter movement assembly (170) is operable to provide the above-described longitudinal advancement and retraction of dilation catheter (120) between the proximal and distal positions. In particular, dilation catheter movement assembly (170) provides such movement by longitudinally sliding along handle (102). Pathway (172) is dimensioned to allow guidewire movement mechanism (160) to longitudinally slide through dilation catheter movement assembly (170). Therefore, guidewire movement mechanism (160) may slide along handle (102) without colliding or interfering with dilation catheter movement assembly (170).

Although dilation catheter movement assembly (170) of the current example is described as sliding along the length of handle (102), movement of dilation catheter (120) can be accomplished by any other suitable operation. In some variations, dilation catheter movement assembly (170) is rotatable relative to handle (102) to provide longitudinal advancement and retraction of dilation catheter (120). Various suitable ways in which dilation catheter (120) may be longitudinally advanced and retracted relative to handle (102) and through the lumen of guide catheter (130) will be apparent to those of ordinary skill in the art in view of the teachings herein.

In the current example, guidewire (150) serves as a substitute for guidewire (50) described above. Guidewire (150) may be configured and operable in accordance with any suitable guidewire known to one skilled in the art including, for example, an illuminating guidewire that is configured to provide a user with confirmation of sinus access via transillumination (e.g., guidewire (50) described above, etc.). For instance, guidewire (150) may include a guidewire support operatively disposed within handle (102) to provide additional column strength to guidewire (150), such that the guidewire support prevents guidewire (150) from buckling within handle (102) during advancement of guidewire (150) relative to handle (102). In some versions, the guidewire support comprises a hypotube. In addition, or in the alternative, guidewire support may be provided by dilation catheter (120).

Guidewire (150) of this example may be inserted through and selectively fixed with a portion of guidewire movement mechanism (160). Guidewire (150) is additionally slideably disposed at least partially in handle (102), in second lumen (123) of dilation catheter (120), and through the open distal end of second lumen (123). Therefore, a portion of guidewire (150) may extend from guidewire movement mechanism (160) through the slot defined by shaft (124), and within second lumen (123) of dilation catheter (120).

During operation of instrument (100), as will be described in greater detail below, guidewire movement mechanism (160) may translate guidewire (150) between a proximal position and a distal position. In particular, guidewire (150) may be longitudinally advanced and retraced relative to handle and through second lumen. When guidewire (150) is in the proximal position, as shown in FIGS. 2 and 4A, guidewire (150) may be positioned to extend past second lumen (123) of dilation catheter (120) and open distal end (132) of guide catheter (130). It should be understood that guidewire (150) may selectively fix with guidewire movement mechanism (160) so that when guidewire (150) is not fixed, guidewire (150) may slide within second lumen (123) while guidewire movement mechanism (160) remains stationary. This may allow an operator to selectively position guidewire (150) to a desired location relative to handle (102). Therefore, the distal tip of guidewire (150) may be positioned within second lumen (123) of dilation catheter (120) and/or within lumen of guide catheter (130) when guidewire (150) is in the proximal position. When guidewire (150) is in the distal position, as shown in FIGS. 4C-4D, guidewire (150) may be positioned distally relative to the distal tip of dilation catheter (120) when dilation catheter (120) is in the distal position.

Guidewire movement mechanism (160) extends from a proximal portion (166) to a distal portion (164). Guidewire movement mechanism (160) includes a coupling slot (168) and a locking and rotation knob (162) rotatably coupled to a proximal finger grip (163). As best seen in FIG. 3, top slot (104) of handle (102) and coupling slot (168) of guidewire movement mechanism (160) complement each other such that guidewire movement mechanism (160) is slidably coupled with handle (102). Additionally, as previously described above, locking and rotation knob (162) is operable to receive and selectively fix guidewire (150). Therefore, guidewire movement mechanism (160) is operable to longitudinally advance and retract guidewire (150) through second lumen (123) of guide catheter (130) by longitudinally sliding guidewire movement mechanism (160) along the length of handle (102) defined by top slot (104).

As best seen in FIG. 2, guidewire (150) is dimensioned to travel through guidewire movement mechanism (160). Guidewire (150) may selectively fix to guidewire movement mechanism (160) via locking and rotation knob (162). Additionally, locking and rotation knob (162) is rotatable about the longitudinal axis defined by the portion of guidewire (150) extending through guidewire movement mechanism (160). Therefore, when guidewire (150) is selectively locked with locking and rotation knob (162), rotation of locking and rotation knob (162) may also rotate guidewire (150) about its own longitudinal axis. Guidewire (150) may have sufficient torsional strength such that rotation of locking and rotation knob (162) also rotates the distal end of guidewire (150). An operator may thus rotate locking and rotation knob (162) to rotate the distal end of guidewire (150) about its own longitudinal axis for accurate placement of guidewire (150).

Although guidewire movement mechanism (160) of the current example is described as sliding along the length of handle (102), movement of guidewire (150) can be accomplished by any other suitable operation. In some variations, guidewire movement mechanism (160) is rotatable relative to handle (102) to provide longitudinal advancement and retraction of guidewire (150). Various suitable ways in which guidewire (150) may be longitudinally advanced and retracted relative to handle (102) and through the second lumen of dilation catheter (120) will be apparent to those of ordinary skill in the art in view of the teachings herein.

FIGS. 4A-4E show an exemplary operation of instrument (100). In FIG. 4A, both guidewire movement mechanism (160) and dilation catheter movement assembly (170) are each in their respective proximal positions as described above. An operator may then insert open distal end (132) of guide catheter (130) into a patent (e.g., via the patient's nostril or mouth, etc.) adjacent to the targeted anatomical passageway (e.g., an ostium or other drainage passageway associated with a paranasal sinus, a Eustachian tube, etc.). It should be understood that guidewire (150) may be selectively coupled with guidewire movement mechanism (160) such that distal tip of guidewire (150) is positioned within guide catheter (130) when guidewire movement mechanism (160) is in its proximal position, as described above.

When guide catheter (130) is placed in its desired location within the patient, an operator may actuate guidewire movement mechanism (160) toward its distal position, thereby actuating the distal tip of guidewire (150) further past the open distal portion (134) of guide catheter (130). It should be understood that an operator may rotate locking and rotation knob (162), either before, during, or after advancement, so the distal end of guidewire (150) rotates about its own longitudinal axis for more accurate placement of guidewire (150). At this point, guide wire (150) may be located within the targeted anatomical passageway, such as a sinus ostium, etc. As described above, body (174) of dilation catheter movement assembly (170) defines a pathway (172) that accommodates translation of guidewire movement mechanism (160). Therefore, it should be understood that translation of guidewire movement mechanism (160) does not affect the longitudinal position of dilation catheter movement assembly (170).

With guidewire (150) advanced to its desired location, an operator may then advance dilation catheter movement assembly (170) toward its distal position, as shown in FIG. 4C. It should be understood that translation of dilation catheter movement assembly (170) also translates dilation catheter (120). Because guidewire (150) is slidably disposed within second lumen (123) of dilation catheter (120), dilation catheter (120) travels over guidewire (150) when dilation catheter movement assembly (170) is advanced. Dilation catheter (120) follows the path defined by the previous advancement of guidewire (150) to place dilation catheter (120) in its desired position within an anatomical passageway of a patient.

With dilation catheter (120) in its desired position within an anatomical passageway of a patient, an operator may then inflate dilator (122) via inflation port (127) to dilate the targeted anatomical passageway of a patient, as shown in FIG. 4E. Inflation may be achieved through any suitable inflation mechanism (e.g., inflator (40)). With the targeted anatomical passageway of the patient dilated, an operator may then retract guidewire (150) while dilator (122) is still in its desired location, as shown in FIG. 4E. An operator may then inject irrigation fluid via irrigation port (128) in order to clear the dilated area of unwanted matter.

In addition to, or as an alternative to, being constructed and operable in accordance with the above teachings, instrument (100) may be constructed and operable in accordance with at least some of the teachings of U.S. Pub. No. 2012/0071856, entitled "Medical Device and Method for Treatment of a Sinus Opening," published Mar. 22, 2012, issued as U.S. Pat. No. 9,554,817 on Jan. 31, 2017, the disclosure of which is incorporated by reference herein. By way of example only, instrument (100) may include a "clicker" and/or other feature that provides audible and/or tactile feedback as knob (162) is rotated to rotate guidewire (150), as described in U.S. Pub. No. 2012/0071856, issued as U.S. Pat. No. 9,554,817 on Jan. 31, 2017. Of course, various other teachings of U.S. Pub. No. 2012/0071856, issued as U.S. Pat. No. 9,554,817 on Jan. 31, 2017, may also be readily incorporated into instrument (100). In addition, or in the alternative, instrument (100) may be modified in accordance with the various teachings below.

III. Exemplary Dilation Catheter Instrument with Automatically Adjusting Fixed Wire System In some instances, it may be desirable to couple guidewire (50, 150) and dilation catheter (20, 120) to unitarily translate together from a proximal position to a first distal position, then automatically break-off so that guidewire (50, 150) is stationary at the first distal position while dilation catheter (20, 120) travels further distally to a second distal position. Additionally, it may subsequently be desirable for guidewire (50, 150) and dilation catheter (20, 120) to re-couple for unitary translation when dilation catheter (20,120) translates back from the second distal position to the first distal position. It may further be desirable to provide for a single finger grip that allows an operator to rotate guidewire (50, 150) and translate guidewire (50, 150) and dilation catheter (20, 120) when dilation catheter (20, 120) and guidewire (50, 150) are coupled. Such a design may simplify use of instrument (100) and prevent guidewire (50, 150) from accidentally hitting sinus walls of a patient.

Figure 5:
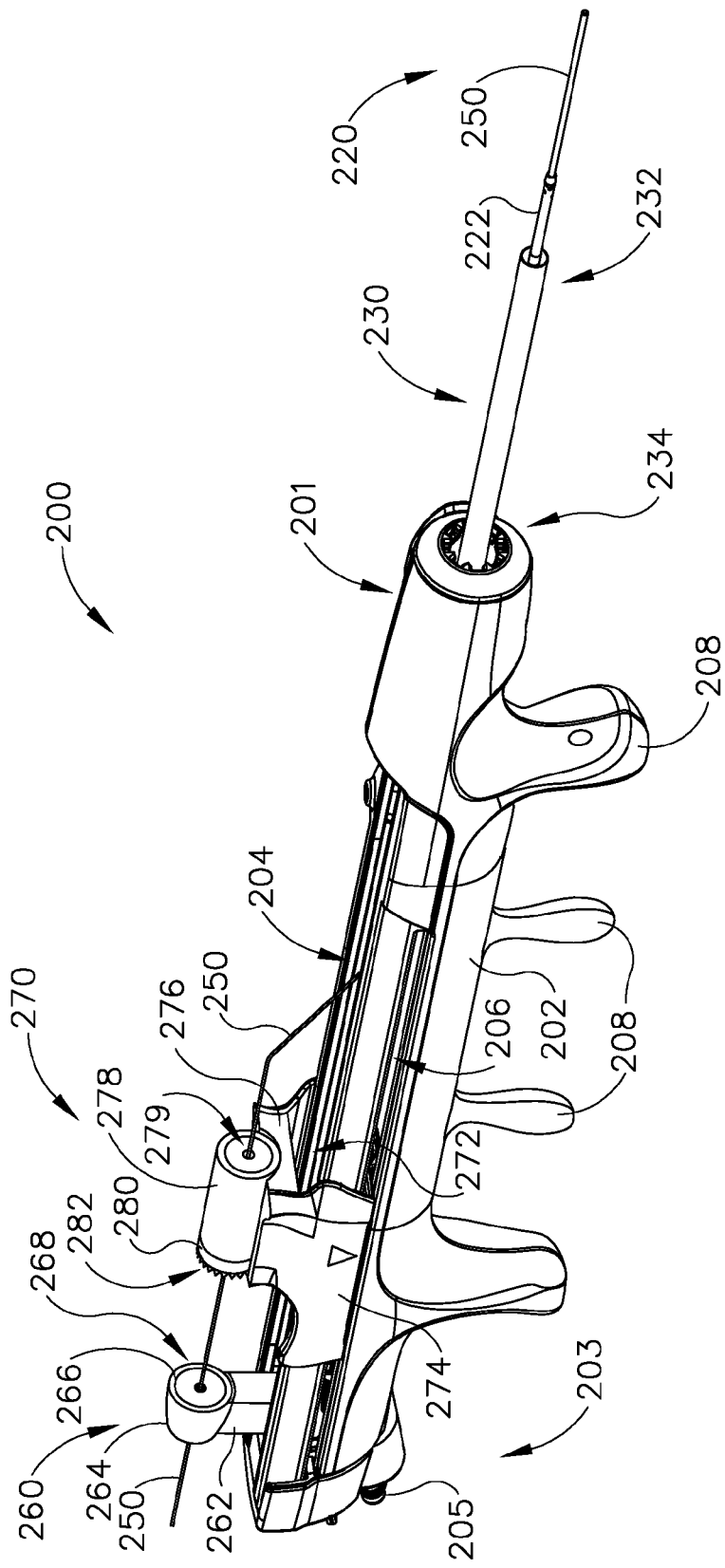
FIG. 5 depicts a perspective view of an alternative instrument suitable for incorporation with the dilation catheter system of FIG. 1.
Figure 6A:
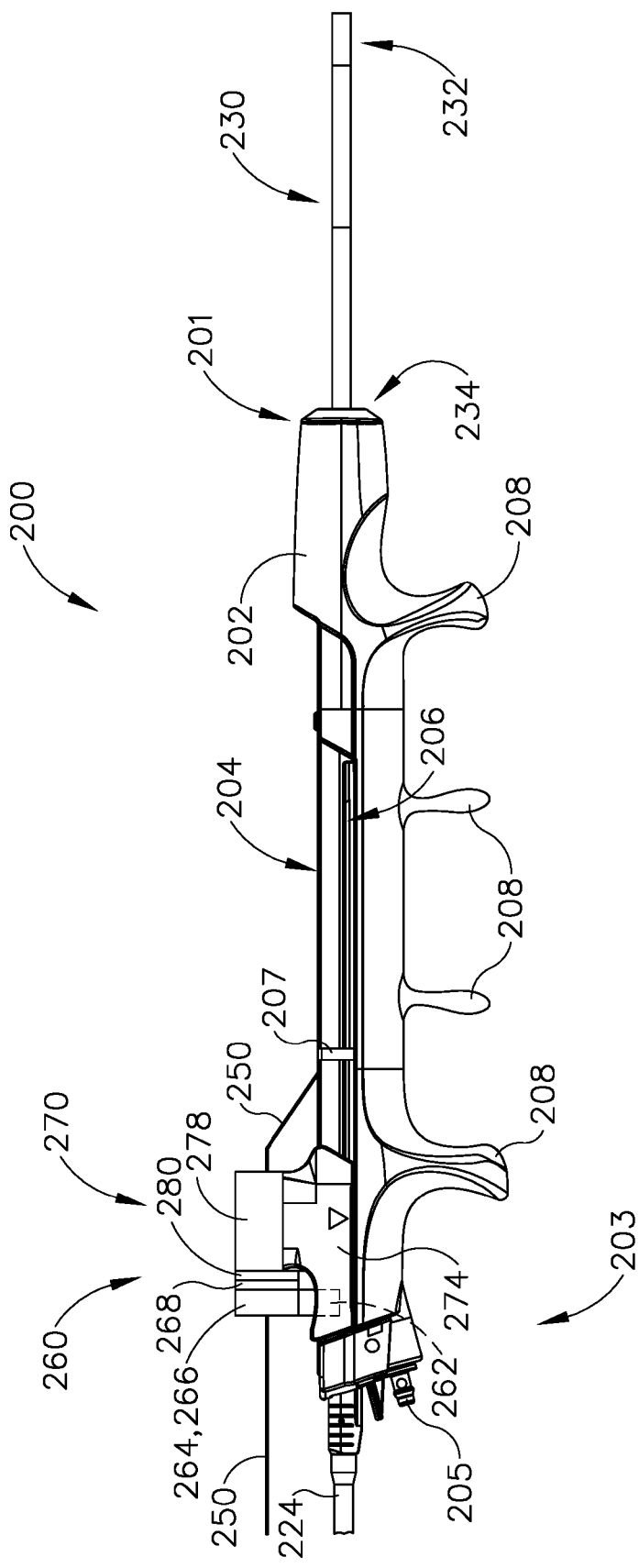
FIG. 6A depicts a side elevational view of the instrument of FIG. 5, with a guidewire and a dilation catheter in a proximal position.
Figure 6B:
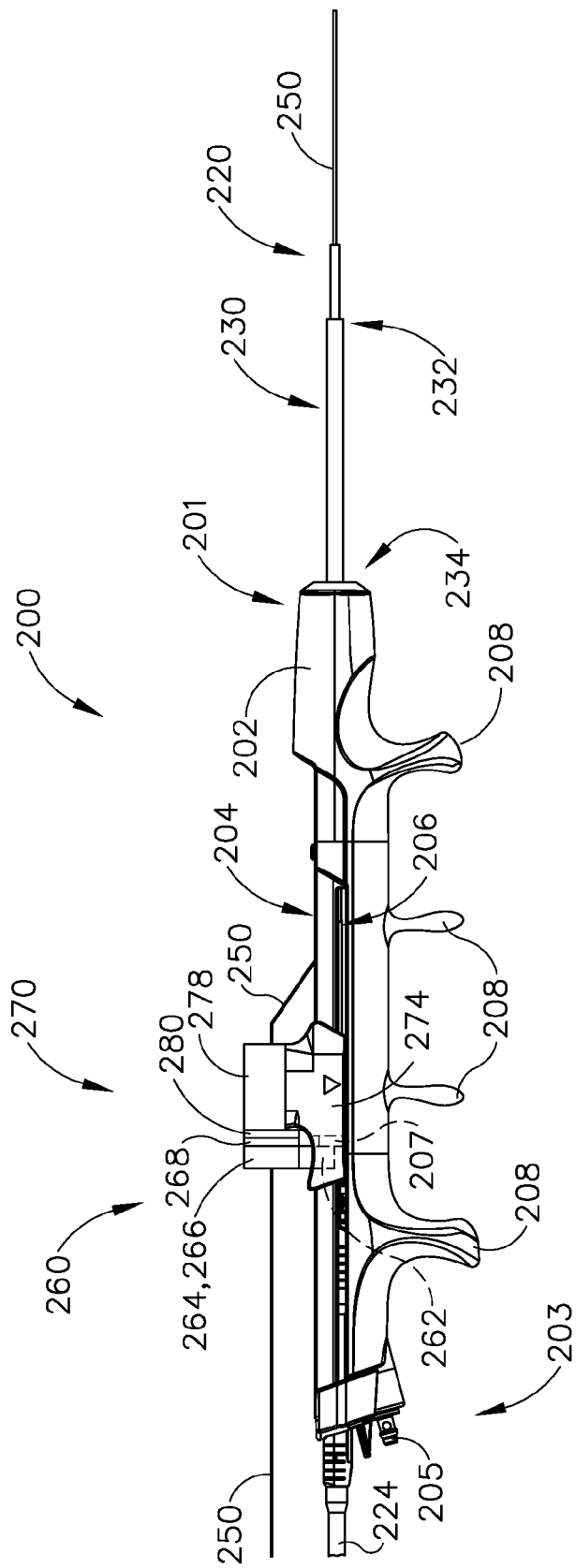
FIG. 6B depicts a side elevational view of the instrument of FIG. 5, with the guidewire of FIG. 6A in a distal position and the dilation catheter of FIG. 6A in an intermediate position.
Figure 6C:
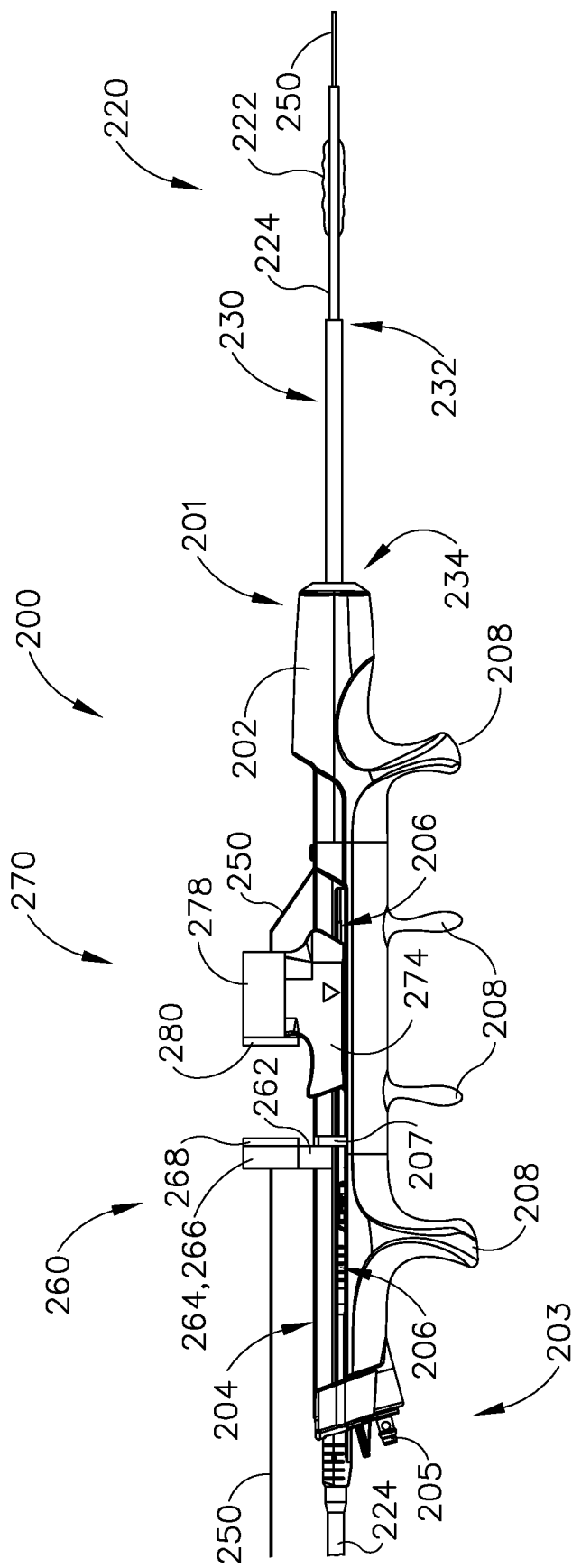
FIG. 6C depicts a side elevational view of the instrument of FIG. 5, with the guidewire of FIG. 6A in a distal position and the dilation catheter of FIG. 6A in a distal position.

FIGS. 5-6C show an exemplary instrument (200) that may be used in place of instrument (100) described above. Therefore, instrument (200) may be used to treat a paranasal sinus drainage passageway (e.g., a frontal recess, a frontal sinus ostium, a maxillary sinus ostium, a sphenoid sinus ostium, etc.) or a Eustachian tube passageway. For instance, instrument (200) may be used to dilate a paranasal sinus drainage passageway. The various features of instrument (200) may be readily incorporated into dilation catheter system (10) discussed above.

Instrument (200) includes a handle (202), a guide catheter (230) removably coupled with handle (202), a dilation catheter (220) slidably housed within both handle (202) and guide catheter (230), a guidewire (250), a guidewire movement mechanism (260), and a dilation catheter movement assembly (270). As will be described in greater detail below, guidewire movement mechanism (260) and dilation catheter movement assembly (270) are configured to couple together to unitarily translate both guidewire (250) and dilation catheter (220) from a proximal position (FIG. 6A) to a first distal position (FIG. 6B), then dilation catheter movement assembly (270) is configured to break free from guidewire movement mechanism (260) in order to further translate dilation catheter (220) along guidewire (250) from the first distal position to a second distal position while guidewire movement mechanism (260) remains in the first distal position (FIG. 6C). As will also be described in greater detail below, dilation catheter movement assembly (270) is configured to rotate guidewire (250) about the longitudinal axis of guidewire (250) while guidewire movement mechanism (260) and dilation catheter movement assembly (270) are coupled together.

Handle (202), guide catheter (230), dilation catheter (220), and guidewire (250) are substantially similar to handle (102), guide catheter (130), dilation catheter (120), and guidewire (150) mentioned above, with differences described below. Therefore, handle (202) of the current example extends from a proximal end (203) to a distal coupling assembly (201) defining a longitudinal axis along the length of handle (202). Handle (202) defines a top slot (204) and a pair to side slots (206), which are substantially similar to top slot (104) and side slots (106) described above. Therefore, top slot (204) is configured to slidably house guidewire movement mechanism (260) while side slots (106) are configured to slidably house dilation catheter movement assembly (270). Additionally, a movable stop (207) is disposed within top slot (204), as best seen in FIGS. 6A-6C. As will be described in greater detail below, moveable stop (207) is configured to be selectively fixed at numerous positions along the length of top slot (204) in order to separate guidewire movement mechanism (260) and dilation catheter movement assembly (270).

Distal coupling assembly (201) is substantially similar to distal coupling assembly (101) described above. Therefore, distal coupling assembly (201) is configured to selectively couple with guide catheter (230) such that a plurality of guide catheters (230) may be separately incorporated into instrument (200).

Handle further includes a fluid port (205) and finger anchoring pegs (208) which are substantially similar to fluid port (105) and finger anchoring pegs (108) described above. Therefore, fluid port (205) is configured to couple with a source of suction to provide suction via guide catheter (130). In addition, or in the alternative, fluid port (205) may be coupled with a fluid source to provide irrigation. Other suitable ways in which fluid port (205) may be made and used will be apparent to those of ordinary skill in the art in view of the teachings herein. Handle (202) is sized and shaped such that instrument (200) can be manipulated and operated by a user (such as a physician) in a convenient and efficient single-handed manner if so desired, with finger anchoring pegs (208) promoting gripping of handle (202) with a single hand. Handle (202) can be formed of any suitable material including, for example, polycarbonate and ABS (acetonitrile butadiene styrene) and can be manufactured using any suitable technique including, for example, injection molding of two clamshell handle halves. Various suitable materials and methods that may be used to manufacture handle (202) will be apparent to those of ordinary skill in the art in view of the teachings herein.

In the current example, guide catheter (230) serves as a substitute for guide catheter (30, 130) described above and shown in FIGS. 1 and 2, respectively. Guide catheter (230) of this example is attached to distal coupling assembly (201) of handle (202) and defines an inner lumen (i.e., inner passage). Guide catheter (230) extends along longitudinal axis defined by handle (202) and has a proximal portion (234) and an open distal end (232). As described above, proximal portion (234) is dimensioned to selectively couple with distal coupling assembly (201) of handle (202).

In the current example, open distal end (232) of guide catheter (230) extends in along a linear path. However, this is merely optional. Open distal end (232) may have any suitable bend or curve along its longitudinal profile that would be apparent to one having ordinary skill in the art in view of the teachings herein. For example, open distal end (232) may have a longitudinal profile similar to that of bent distal end (32) of guide catheter (30) described above. It should be understood that since guide catheter (230) is capable of selectively coupling with distal coupling assembly (201) of handle (202), an operator may attach a guide catheter having desired dimensions, including longitudinal profile, in order to access a desired location within a patient, such as a specific paranasal sinus ostium or other anatomical passageway. Various suitable dimensions and longitudinal profiles will be apparent to one having ordinary skill in the art in view of the teachings herein.

Dilation catheter (220) may be substantially similar to dilation catheter (120) described above, with differences described below. Dilation catheter (220) includes a dilator (222) and a shaft (224) substantially similar to dilator (122) and shaft (124) described above. Therefore, dilation catheter (220) may translate along guidewire (250) and within guide catheter (230) from a proximal position, where dilator (222) is proximal relative to open distal end (232); to a distal position, where dilator (222) is distal relative to open distal end (232). Further, dilator (222) may expand to a dilated state in order to dilate a targeted anatomical passageway. Shaft (224) may have three lumens substantially similar to lumens (121, 123, 125) described above, each having substantially the same function as described above. Therefore, a first lumen may be used to inflate dilator (222), while a second lumen may be used to slidingly receive guidewire (250), and a third lumen may be used to transfer irrigation fluid to the surgical site via the distal end of shaft (224). Dilation catheter (220) may include a manifold, inflation port, and irrigation port, substantially similar to manifold (126), inflation port (127), and irrigation port (128) described above.

Dilation catheter movement assembly (270) includes a body (274) defining a pathway (272), a saddle (276) rotatably supporting a rotary finger grip (278), and a proximal coupling end (280) unitarily attached to rotating finger grip (278). Additionally, proximal coupling end (280) includes a rotational transfer member (282) proximally presented toward guidewire movement mechanism (260). Similar to body (174), body (274) extends into side slots (206) of handle (202) in order to slidably couple with handle (202). Body (274) is also fixed to shaft (224) of dilation catheter (220). Therefore, dilation catheter movement assembly (270) is operable to provide longitudinal advancement and retraction of dilation catheter (220) between a proximal position (FIG. 6A), a first distal position (FIG. 6B), and a second distal position (FIG. 6C). In particular, dilation catheter movement assembly (270) provides such movement by longitudinally sliding along handle (202).

Unlike pathway (172) of instrument (100), pathway (272) of dilation catheter movement assembly (270) is not dimensioned to allow guidewire movement mechanism (260) to longitudinally slide through dilation catheter movement assembly (270). Instead, pathway (272) is dimensioned to allow dilation catheter movement assembly (270) to slide over movable stop (207). Therefore, dilation catheter movement assembly (270) is configured to slide along handle (202) regardless of where movable stop (207) is longitudinally located within top slot (204).

Rotating finger grip (278) is configured is rotatably couple to saddle (276) such that rotating finger grip (278) may rotate about its own longitudinal axis relative to the rest of dilation catheter movement assembly (270). Additionally, rotating finger grip (278) may not translate relative to the rest of dilation catheter movement assembly (270). In other words, a user may spin rotating finger grip (278) in order to rotate finger grip (278) about its own longitudinal axis; and a user may push finger grip (278) distally or proximally in order to translate all of dilation catheter movement assembly (270) within top slot (204) along handle (202). Any suitable features may be added to rotating finger grip (278) and/or saddle (276) as would be apparent to one having ordinary skill in the art in view of the teachings herein.

Rotating finger grip (278) and proximal coupling end (280) define a longitudinal pathway (279). Longitudinal pathway (279) is dimensioned to slidingly receive guidewire (250) without fixing to or interfering with guidewire (250). As will be described in greater detail below, rotating finger grip (278) is configured to selectively couple with guidewire movement mechanism (260) via proximal coupling end (280), rotational transfer member (282), and distal coupling end (268) in order to help actuate guidewire (250) and rotate guidewire (250) about its own longitudinal axis.

Guidewire movement mechanism (260) includes a slide (262), a rotational bearing (264), a guidewire coupler (266), and a distal coupling end (268). Slide (262) is slidably housed within top slot (204) of handle (202). Slide (262) is dimensioned to contact movable stop (207) within top slot (204) in order to prevent guidewire movement mechanism (260) from further distal translation, therefore breaking a coupling between dilation catheter movement assembly (270) and guidewire movement mechanism (260).

Rotational bearing (264), guidewire coupler (266), and distal coupling end (268) are unitarily connected, while rotational bearing (264) is rotationally coupled with slide (262). Rotational bearing (264), guidewire coupler (266), and distal coupling end (268) are configured to unitarily rotate relative to slide (262) along the same rotational axis of rotating finger grip (278). While in the current example, a rotational bearing (264) is used to rotationally couple guidewire coupler (266) and slide (262), any other suitable structure may be used as would be apparent to one having ordinary skill in the art in view of the teachings herein.

Guidewire coupler (266) is configured to receive and selectively fix to guidewire (250). Therefore, a user may insert guidewire (250) through guidewire coupler (266), longitudinal pathway (279), portions of handle (202), and shaft (224) of dilation catheter (220) until the distal end of guidewire (250) is at its desired position. Then a user may fix guidewire coupler (266) to guidewire (250) such that translation of guidewire coupler (266) leads to translation of guidewire (250), and such that rotation of guidewire coupler (266) leads to rotation of guidewire (250). In other words, rotational bearing (264) and guidewire coupler (266) may rotate guidewire (250) about the longitudinal axis of guidewire (250) as well as longitudinally translate guidewire (250).

As described above, and as will be described in greater detail below, dilation catheter movement assembly (270) and guidewire movement mechanism (260) are configured to selectively couple and decouple with each other. When coupled, dilation catheter movement assembly (270) and guidewire movement mechanism (260) are configured to unitarily translate. Additionally, when coupled, rotation of rotating finger grip (278) relative to saddle (276) will rotate guidewire coupler (266), and therefore guidewire (250), about the longitudinal axis of guidewire (250).

In particular, proximal coupling end (280) of dilation catheter movement assembly (270) and distal coupling end (268) of guidewire movement mechanism (260) are positioned to mate with each other in order to couple dilation catheter movement assembly (270) and guidewire movement mechanism (260). The coupling between proximal coupling end (280) and distal coupling end (268) may be accomplished through a variety of suitable ways known to one having ordinary skill in the art in view of the teachings herein. For instance, proximal coupling end (280) and distal coupling end (268) may comprise complementary magnets, which provide sufficient coupling force when proximal coupling end (280) and distal coupling end (268) are sufficiently close enough to one another. Alternatively, proximal coupling end (280) and distal coupling end (268) may couple with each other through a clicking press fit combination, such that proximal coupling end (280) and distal coupling end (268) snap fit into and out of coupling with each other.

Coupling forces between proximal coupling end (280) and distal coupling end (268) are strong enough such that user may distally translate dilation catheter movement assembly (270), which in turn pulls guidewire movement mechanism (260) (as shown in between FIGS. 6A-6B). Therefore, when dilation catheter movement mechanism (270) and guidewire movement mechanism (260) are coupled, a user may only be required to manipulate dilation catheter movement assembly (270) in order to unitarily translate both guidewire (250) and dilation catheter (220) at the same time.

As described above, rotating finger grip (278) is also configured to rotate guidewire (250) about its own longitudinal axis when dilation catheter movement assembly (270) and guidewire movement mechanism (260) are coupled. In particular, rotational transfer member (282) may include grooves or ridges that act as teeth when proximal coupling end (280) is coupled with distal coupled end (268). Therefore, rotational transfer member (282) may help ensure that when a user rotates rotating finger grip (278) relative to saddle (276), the rotational motion is transferred to guidewire coupler (266) and rotational bearing (264) in order to rotate guidewire (250) about its own longitudinal axis. Of course, in some instances, the coupling force generated between proximal couple end (280) and distal coupling end (268) may be strong enough such that rotational transfer member (282) is not needed. Therefore, it should be understood that rotational transfer member (282) is merely optional. In the current example, rotational transfer member (282) is shown as an element of proximal coupling end (280). However, a portion or the entirety of rotational transfer member (282) may be incorporated into guidewire movement mechanism (260).

As described above, it may be desirable to select a location along the length of handle (202) to decouple dilation catheter movement assembly (270) and guidewire movement mechanism (260) such that dilation catheter movement assembly (270) may further translate distally while guidewire movement mechanism (260) remains stationary. This selected decoupling may allow for dilation catheter (220) to travel distally while guidewire (250) remains stationary. If the distal end of guidewire (250) is distal in relation to the distal end of dilation catheter (220) when dilation catheter movement assembly (270) and guidewire movement mechanism (260) decouple, dilation catheter (220) may slide over guidewire (250) when dilation catheter (220) translates relative to guidewire (250).

As mentioned above, moveable stop (207) may be selectively fixed along the length of handle (202) defining top slot (204). Moveable stop (207) determines the location at which further distal translation of dilation catheter movement assembly (270) will decouple dilation catheter movement assembly (270) with guidewire movement mechanism (260). As mentioned above, dilation catheter movement assembly (270) defines a pathway (272) which accommodates moveable stop (207) such that dilation catheter movement assembly (270) may translate along the length of handle (202) without contacting movable stop (207). Additionally, moveable stop (207) is positioned within top slot (204) of handle (202), the same slot which slide (262) of guidewire movement mechanism (260) is located. Therefore, when guidewire movement mechanism (260) and dilation catheter movement assembly (270) are unitarily translated from a proximal position (FIG. 6A) to a first distal position (FIG. 6B), slide (262) of guidewire movement mechanism (260) contacts movable stop (207) while dilation catheter movement assembly (270) does not. If a user tries to slide dilation catheter movement assembly (270) further in the distal direction while moveable stop (207) contacts guidewire movement assembly (260), the contact between movable stop (207) and slide (262) is strong enough to decouple guidewire movement mechanism (260) and dilation catheter movement assembly (270). Once decoupled, dilation catheter movement assembly (270) may further translate distally within handle (202). Guidewire (250) is still slidably disposed within longitudinal pathway (279). However, once dilation catheter movement assembly (270) and guidewire movement mechanism (260) are decoupled, rotation of finger grip (278) no longer rotates guidewire (250) about its own longitudinal axis.

Movable stop (207) may be selectively fixed along the length of handle (202) by any suitable means apparent to one having ordinary skill in the art in view of the teachings herein. For example, a set screw, latching feature, or braking feature may be used to fix moveable stop (207). Alternatively, stop (207) may be selectively held in place due to friction from an interference fitting, friction from an elastomeric material, and/or in any other suitable fashion.

FIG. 6A-6C show instrument (200) in exemplary use. In FIG. 6A, dilation catheter movement assembly (270) and guidewire movement mechanism (260) are in the proximal position and coupled together via proximal coupling end (280) and distal coupling end (268). At this point, a user may rotate finger grip (278) in order to rotate guidewire (250) about its own longitudinal axis for more accurate placement of guidewire (250). A user may insert guide catheter (230) into a patient such that open distal end (232) is at a location adjacent to a targeted anatomical passageway, such as a paranasal sinus ostium or a Eustachian tube, etc.

Once guide catheter (230) is at its desired location, a user may slide both dilation catheter movement assembly (270) and guidewire movement mechanism (260) to the first distal location shown in FIG. 6B by translating finger grip (278) in the distal direction. At the stage shown in FIG. 6B, the distal end of guidewire (250) may be positioned within its desired location in the anatomical passageway of a patient. While guidewire movement mechanism (260) and dilation catheter movement assembly (270) are still coupled, a user may rotate rotating finger grip (278) about its longitudinal axis in order to rotate rotational bearing (264) and guidewire coupler (266), thereby rotating guidewire (250) about its own longitudinal axis.

With guidewire (250) placed in its desired location (as shown in FIG. 6B), a user may further distally translate dilation catheter movement assembly (270) to a second distal location (FIG. 6C) such that dilator (222) is in the desired location within the anatomical passageway of a patient. At this point, dilation catheter movement assembly (270) and guidewire movement mechanism (260) are decoupled due to interference provided by moveable stop (207). Guidewire (250) is stationary while distal movement of dilation catheter transfer member (270) causes distal movement of dilation catheter (220) along stationary guidewire (250), as shown between FIG. 6B and FIG. 6C. If a user rotates finger grip (278) while dilation catheter transfer member (270) and guidewire movement mechanism (260) are decoupled, guidewire (250) will not rotate because finger grip (278) is not coupled with guidewire coupler (266).

With dilation catheter (222) in the desired location, a user may inflate dilator (222) in order to dilate the targeted anatomical passageway. With the anatomical passageway dilated, a user may deflate dilator (222) and retract dilator movement assembly (270) from the position shown in FIG. 6C to the position shown in FIG. 6B. Dilator catheter (220) travels along stationary guidewire (250) until guidewire movement mechanism (260) and dilation catheter movement assembly (270) recouple. Then, a user may further translate both guidewire movement mechanism (260) and dilation catheter movement assembly (270) in the proximal direction from the position shown in FIG. 6B to the position shown in FIG. 6A. Guidewire (250) and dilation catheter (222) unitarily travel with each other while being retracted from the position shown in FIG. 6B to the position in FIG. 6A.

IV. Exemplary Dilation Catheter Instrument with Rapid Guidewire Confirmation Device In some instances, it may be difficult to place guidewire (50, 150, 250) in the targeted anatomical passageway of a patient, such as an ostium (O). It may require multiple attempts of guidewire (50, 150, 250) actuating back-and-forth (i.e., "fishing") until guidewire (50, 150, 250) is advanced to its desired location. This may take up valuable procedure time. Therefore, it may be desirable to decrease the attempts of actuating guidewire (50, 150, 250) back-and-forth until guidewire (50, 150, 250) is advanced to its desired location. It may further be desirable to automate the fishing process of advancing and retracting guidewire (50, 150, 250) until guidewire (50, 150, 250) is advanced to its desired location.

FIGS. 7A-7L show an instrument (300) configured to automatically actuate guidewire (350) back-and-forth until the distal end of guidewire (350) is placed within the targeted anatomical passageway. Instrument (300) includes a handle (302), a dilation catheter (320), a guide catheter (330), a guidewire movement mechanism (360), a dilation catheter movement actuator (370), and a guidewire placement confirmation assembly (380).

Handle (302) defines a slot (304) that slidingly houses portions of guidewire movement mechanism (360) and dilation catheter movement actuator (370). While not shown, it should be understood handle (302) may include various features of handle (102, 202) described above, such as additional slots, fluid ports (105, 205), anchoring pegs (108, 208), and distal coupling assembly (101, 201). Handle (302) is sized and shaped such that instrument (300) can be manipulated and operated by a user (such as a physician) in a convenient and efficient single-handed manner if so desired. Handle (302) can be formed of any suitable material including, for example, polycarbonate and ABS (acetonitrile butadiene styrene) and can be manufactured using any suitable technique including, for example, injection molding of two clamshell handle halves. Various suitable materials and methods that may be used to manufacture handle (302) will be apparent to those of ordinary skill in the art in view of the teachings herein.

Guide catheter includes a proximal portion (334) and a bent distal portion (332) having an open end. In the current example, proximal portion (334) is fixed to handle (302). However, proximal portion (334) may be selectively coupled to handle (302), as described above for guide catheter (130, 230). Guide catheter (330) defines an inner lumen (i.e., inner passage). Guide catheter (330) extends along longitudinal axis defined by handle (302) and curves at bent distal portion (332). Bent distal portion (332) may have any suitable bend that would be apparent to one having ordinary skill in the art in view of the teachings herein; or may even be straight.

Dilation catheter (320) comprises a dilator (322) and a shaft (324). Similar to dilation catheter (120, 220) described above, dilation catheter (320) is configured to slide within handle (302) and guide catheter (330) in order to place dilator (322) within a targeted anatomical passageway. Shaft (324) is coupled to dilation catheter movement actuator (370), which is configured to slide along slot (304) in order to actuate dilation catheter (320) as will be described in greater detail below. Shaft (324) may be substantially similar to shaft (124, 224) described above. Therefore, shaft (334) may define multiple lumens to perform similar functions as lumens (121, 123, 125) described above. Therefore, shaft (334) may slidingly receive guidewire (330) as well as inflate and deflate dilator (322) through separate lumens.

Dilation catheter movement assembly (370) includes a slide (372) housed within slot (304), and a coupler (374) fixed to both slide (372) and shaft (324) of dilation catheter (320). Dilation catheter movement assembly (370) may include any suitable features of dilation catheter movement assembly (170, 270) described above, as would be apparent to one having ordinary skill in the art in view of the teachings herein. Longitudinal translation of slide (372) results in direct longitudinal translation of dilation catheter (320) via coupler (374). A user may therefore push/pull slide (372) manually with their hand in order to actuate dilation catheter (320) relative to handle (302) and guide catheter (330), similar to actuation of dilation catheter (120, 220) described above.

Guidewire movement mechanism (360) includes a slide (362) housed within slot (304) proximal in relation to slide (372), and a coupler (364) extending from slide (362) and fixed to guidewire (350). Guidewire movement mechanism (360) may include any combination of suitable features from guidewire movement mechanism (160, 260) described above as would be apparent to one having ordinary skill in the art in view of the teachings herein. Longitudinal translation of slide (362) results in direct longitudinal translation of guidewire (350) via coupler (364). A user may therefore push/pull slide (362) manually with their hand in order to actuate guidewire (350) relative to handle (302) and guide catheter (330), similar to actuation of guidewire (150, 250) described above. Additionally, as will be described in greater detail below, guidewire placement confirmation assembly (380) may automatically actuate guidewire (350) in a back-and-forth fishing motion until guidewire (350) has actuated distally to a predetermined distance.

Guidewire placement confirmation assembly (380) includes a control module (382), an actuation assembly (384), an activation input (385) disposed on the exterior of handle (302), a rod (386) driven by actuation assembly (384), a force transducer (388) connected to guidewire (350), and a power source (390). Control module (382) is in communication with actuation assembly (384), activation input (385), force transducer (388), and power source (390) via wires (392). Control module (382) is powered by power source (390), which also powers force transducer (388), actuation assembly (384), and actuation input (385). As will be described in greater detail below, control module (382) is operable to receive input from activation input (385), force transducer (388), and actuation assembly (384) in order to command actuation assembly (384) to drive guidewire (350) and guidewire movement mechanism (360) until the distal end of guidewire (350) is placed within the targeted anatomical passageway of a patient.

One end of rod (386) is coupled with actuation assembly (384). As described above, actuation assembly (384) is capable of driving rod (386) distally and proximally. The other end of rod (383) is fixed to coupler (364) of guidewire movement mechanism (360) such that when actuation assembly (384) drives rod (386), rod (386) drives guidewire movement mechanism (360) and guidewire (350). Therefore, actuation assembly (384) is capable of actuating guidewire (350) distally and proximally in a back-and-forth reciprocating motion.

Actuation assembly (384) may determine and communicate the longitudinal location of rod (386), and therefore the longitudinal location of guidewire (350), to control module (382). Actuation assembly (384) may determine the longitudinal location of rod (386) through any suitable means known to a person having ordinary skill in the art in view of the teachings herein, such as linear transducers. Control module (382) may use the longitudinal location of guidewire (350) and compare it to a predetermined longitudinal location indicative of the distal end of guidewire (350) being inserted into the targeted anatomical passageway. If the longitudinal location of guidewire (350) is equal to the predetermined longitudinal location, control module (382) may deactivate actuation assembly (384). Actuation assembly (384) and rod (386) may have any suitable components that would be apparent to one having ordinary skill in the art in view of the teachings herein. While in the current example, rod (386) is fixed to coupler (364), rod (386) may be connected to any other suitable element in order to actuate guidewire (350) back-and-forth as would be apparent to one having ordinary skill in the art in view of the teachings herein.

Force transducer (388) is coupled to guidewire (350). Force transducer (388) is configured to measure the external forces experienced by the distal end of guidewire (350) and to communicate that external force to control module (382). As will be described in greater detail below, control module (382) may utilize this information from force transducer (388) to determine whether to continue actuating rod (386) distally or to actuate rod (386) proximally. In particular, force transducer (388) may measure a force exerted on the distal end of guidewire (350) experienced by hitting anatomy of a patient indicative of missing the targeted anatomical passageway. If control module (382) receives a signal from force transducer (388) indicative of the distal end of guidewire (350) missing the targeted anatomical passageway, control module (382) may command actuation assembly (384) to actuate rod (386) proximally back to a starting position or back within guide catheter (330) in order to restart an actuation cycle of fishing guidewire (350).

Control module (382) may be programmed to deactivate guidewire placement confirmation assembly (380) if actuation assembly (384) has completed a predetermined amount of actuation cycles. Therefore, if a user fails to find the targeted anatomical passageway, they may safely remove instrument (300) from a patient or decide to reactivate guidewire placement confirmation assembly (380). If control module (382) receives a signal from force transducer (388) that is not indicative of missing the targeted anatomical passageway, control module (382) may command actuation assembly (384) to continue actuating rod (386) until guidewire (350) reaches the predetermined longitudinal location, as described above. Then, a user may then further advance guidewire (350) to its desired location manually via slide (362) and perform the rest of the procedure.

Activation input (385) is configured to allow a user to generate a set of predetermined parameters and send those parameters to control module (382). Additionally, activation input (385) is configured to activate guidewire placement confirmation assembly (380), as will be described in greater detail below. Activation input (385) may contain any suitable components as would be apparent to one having ordinary skill in the art in view of the teachings herein. For example, activation input (385) may have a touchscreen, a plurality of buttons, etc. Control module (382) is configured to store the predetermined parameters and to activate actuation assembly (384) in response to user commands generated from activation input (385). A predetermined force, a predetermined distance, and a predetermined actuation cycle threshold may be just come of the predetermined parameters that activation input (385) may generate and send control module (382). Any other suitable predetermined parameters will be apparent to one having ordinary skill in view of the teachings herein.

In particular, control module (382) may control actuation assembly (384) to advance guidewire (350) distally until guidewire (350) encounters the predetermined force or guidewire (350) travels the predetermined distance. If guidewire (350) encounters the predetermined force before traveling the predetermined distance, control module (382) may instruct actuation assembly (384) to retract guidewire (350) proximally within guide catheter (330) or any other suitable distance and then advance guidewire (350) back toward the predetermined distance to start another actuation cycle. If guidewire (350) travels the predetermined distance, actuation assembly (384) may stop actuating guidewire (350), which may indicate to a user that guidewire (350) has been placed within the targeted anatomical passageway of a patient. The predetermined distance may be indicative of the distal end of guidewire (350) entering the targeted anatomical passageway while the predetermined force may be indicative of the distal end of guidewire (350) contacting anatomy of a patient adjacent to the targeted anatomical passageway, therefore missing the anatomical passageway.

Figure 7A:
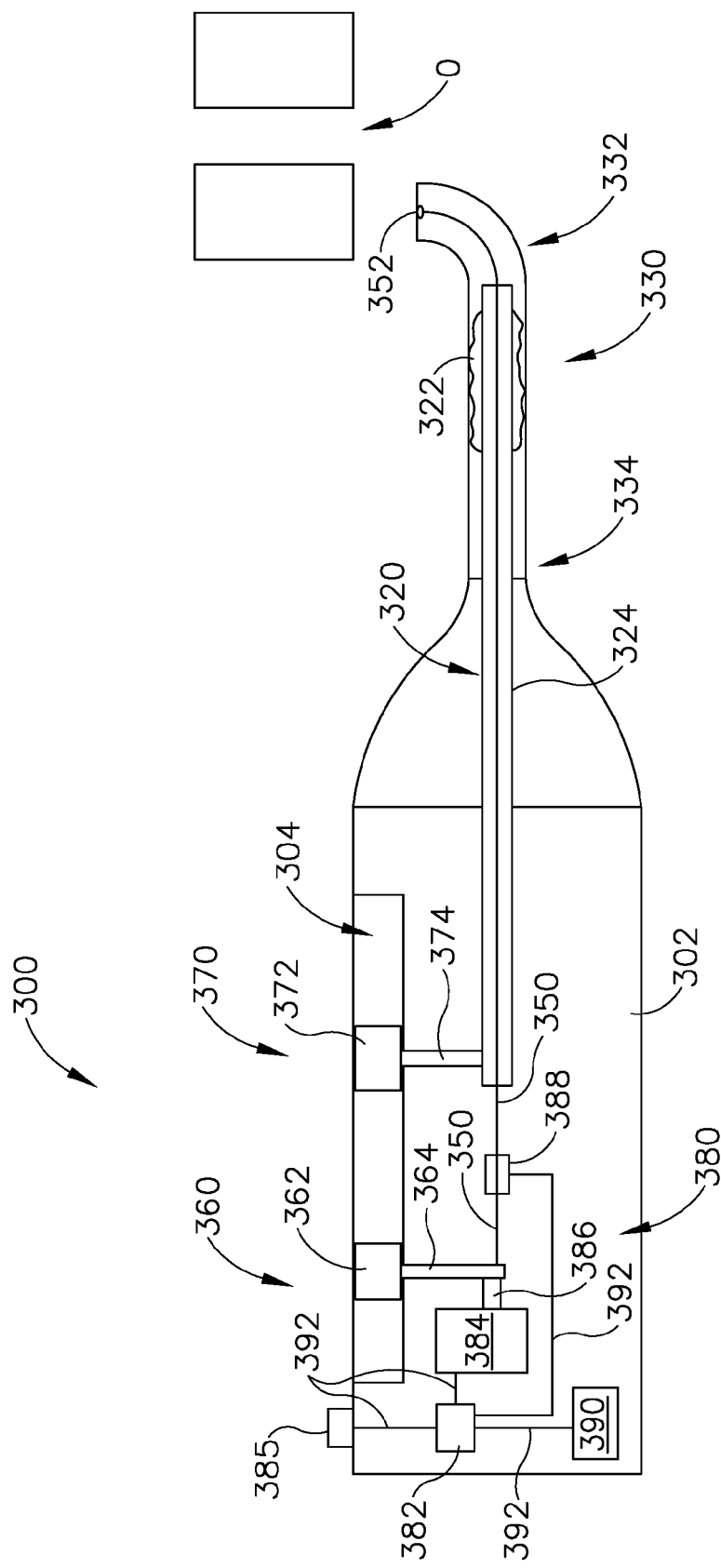
FIG. 7A depicts a side schematic view of an alternative instrument suitable for incorporation with the dilation catheter system of FIG. 1, where a distal portion of a guide catheter is positioned proximally in relation to a targeted ostium of a patient and a guidewire is within the guide catheter.

FIGS. 7A-7L show exemplary use of instrument (300) described above. FIG. 7A shows instrument positioned such that the open end of bent distal portion (332) of guide catheter (230) is proximal in relation to an ostium (O) of a patient. It should be understood that both the distal end of guidewire (330) and the distal end of dilation catheter (320) are within bent distal portion (332) of guide catheter (330).

Figure 7B:
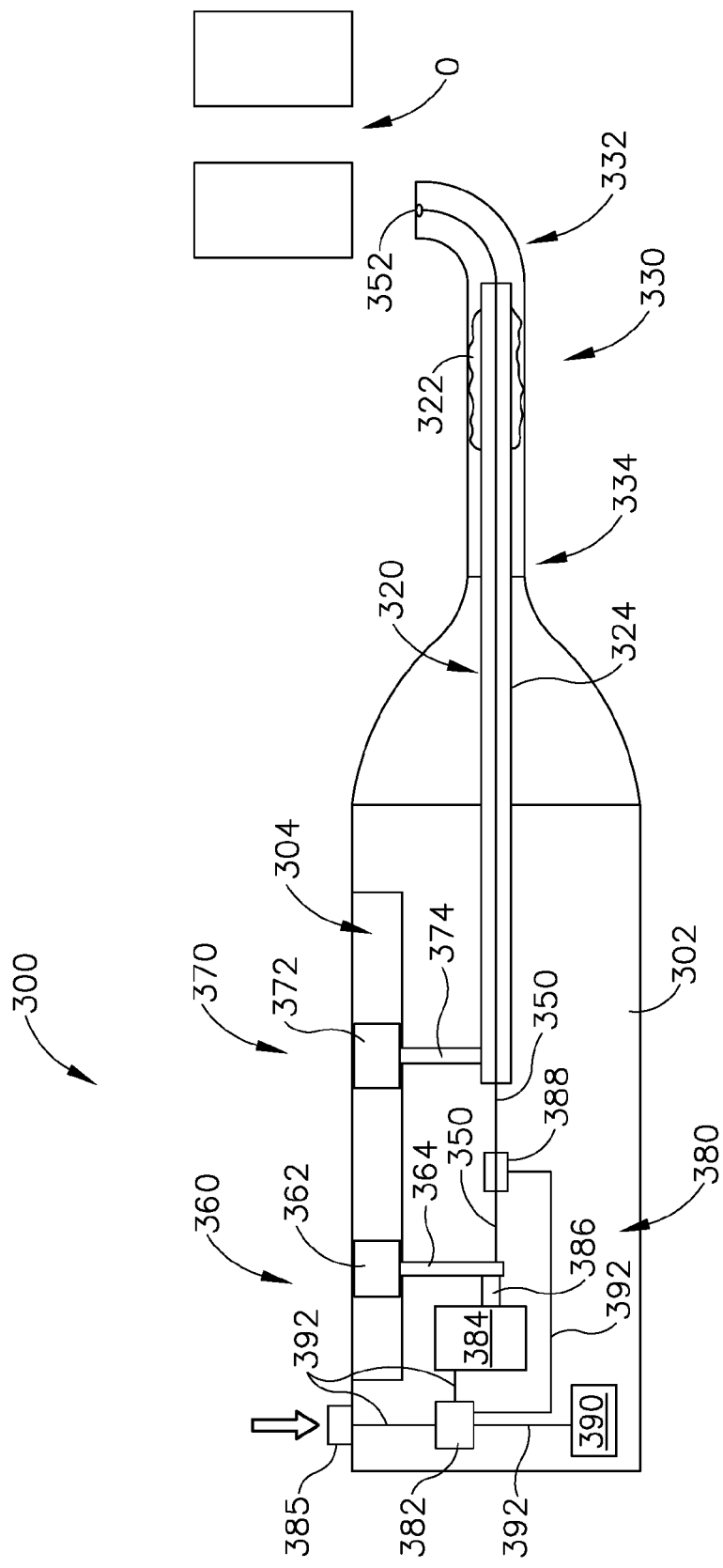
FIG. 7B depicts a side schematic view of the instrument of FIG. 7A, where the distal portion of the guide catheter of FIG. 7A is positioned proximally in relation to a targeted ostium of a patient and the guidewire of FIG. 7A is within the guide catheter.

Next, as shown in FIG. 7B, a user may input all the necessary parameters, similar to the parameter mentioned above, and activate guidewire placement confirmation assembly (380). It should be understood that some or all the necessary parameters may be preloaded into control module (382).

Figure 7C:
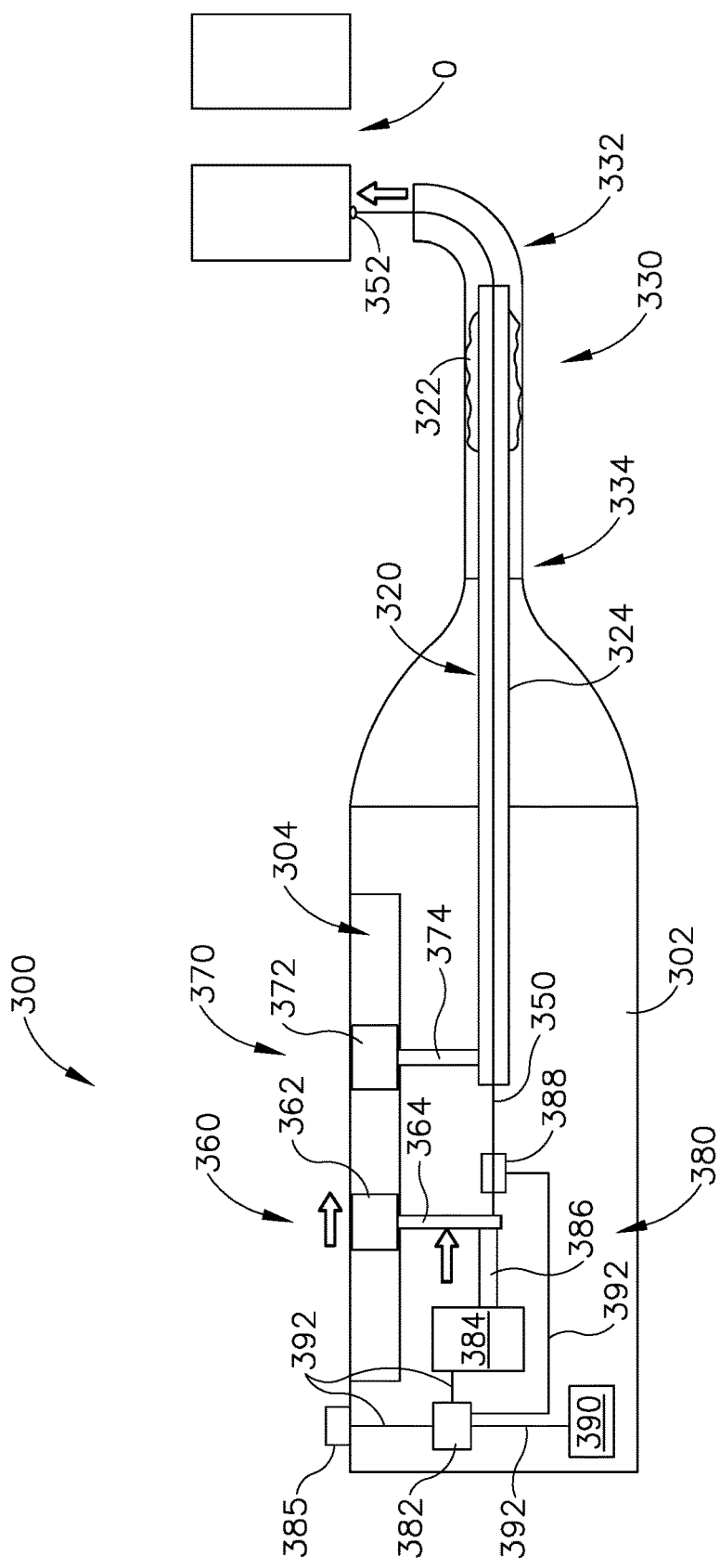
FIG. 7C depicts a side schematic view of the instrument of FIG. 7A, where the distal portion of the guide catheter of FIG. 7A is positioned proximally in relation to a targeted ostium of a patient and the guidewire of FIG. 7A has exited the distal portion of the guide catheter.
Figure 7D:
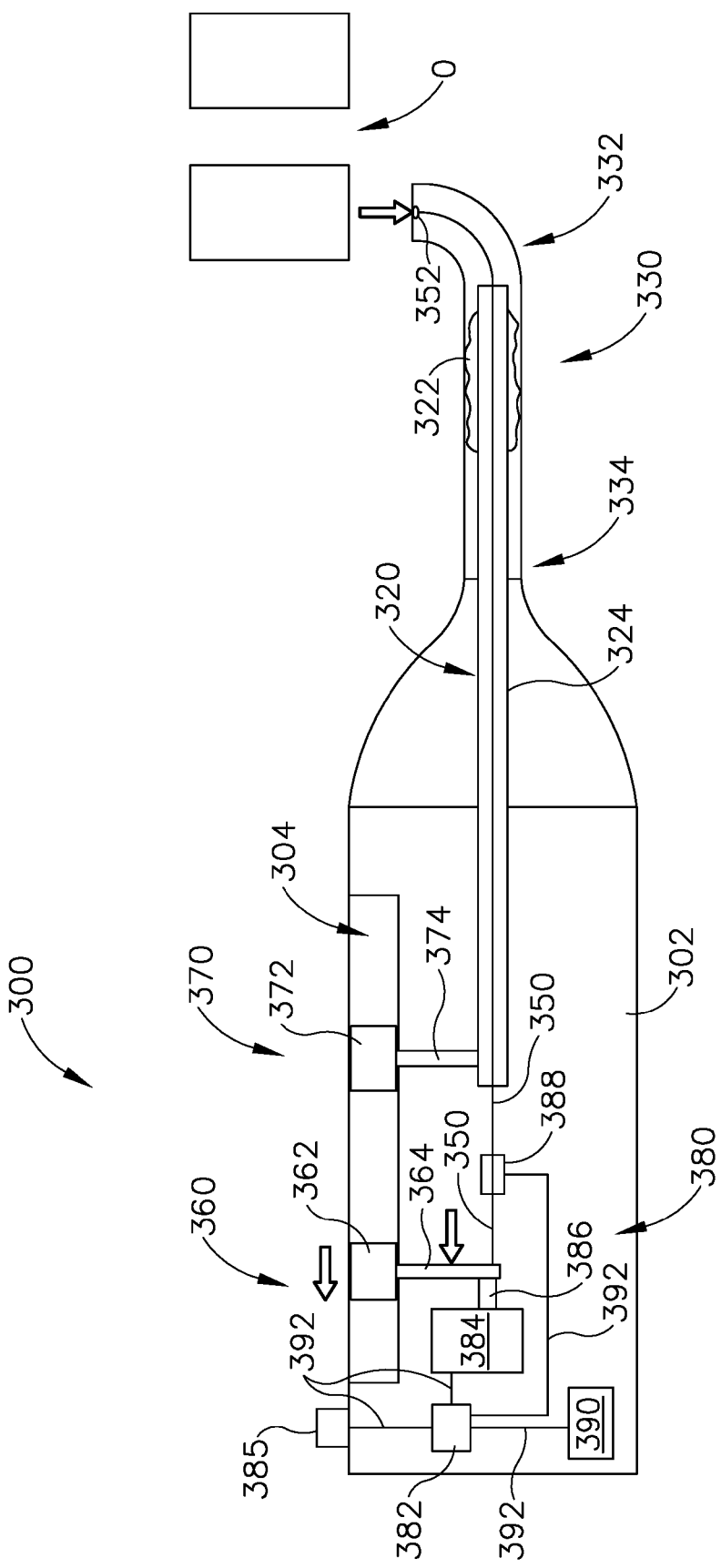
FIG. 7D depicts a side schematic view of the instrument of FIG. 7A, where the distal portion of the guide catheter of FIG. 7A is positioned proximally in relation to a targeted ostium of a patient and the guidewire of FIG. 7A is within the guide catheter.
Figure 7E:
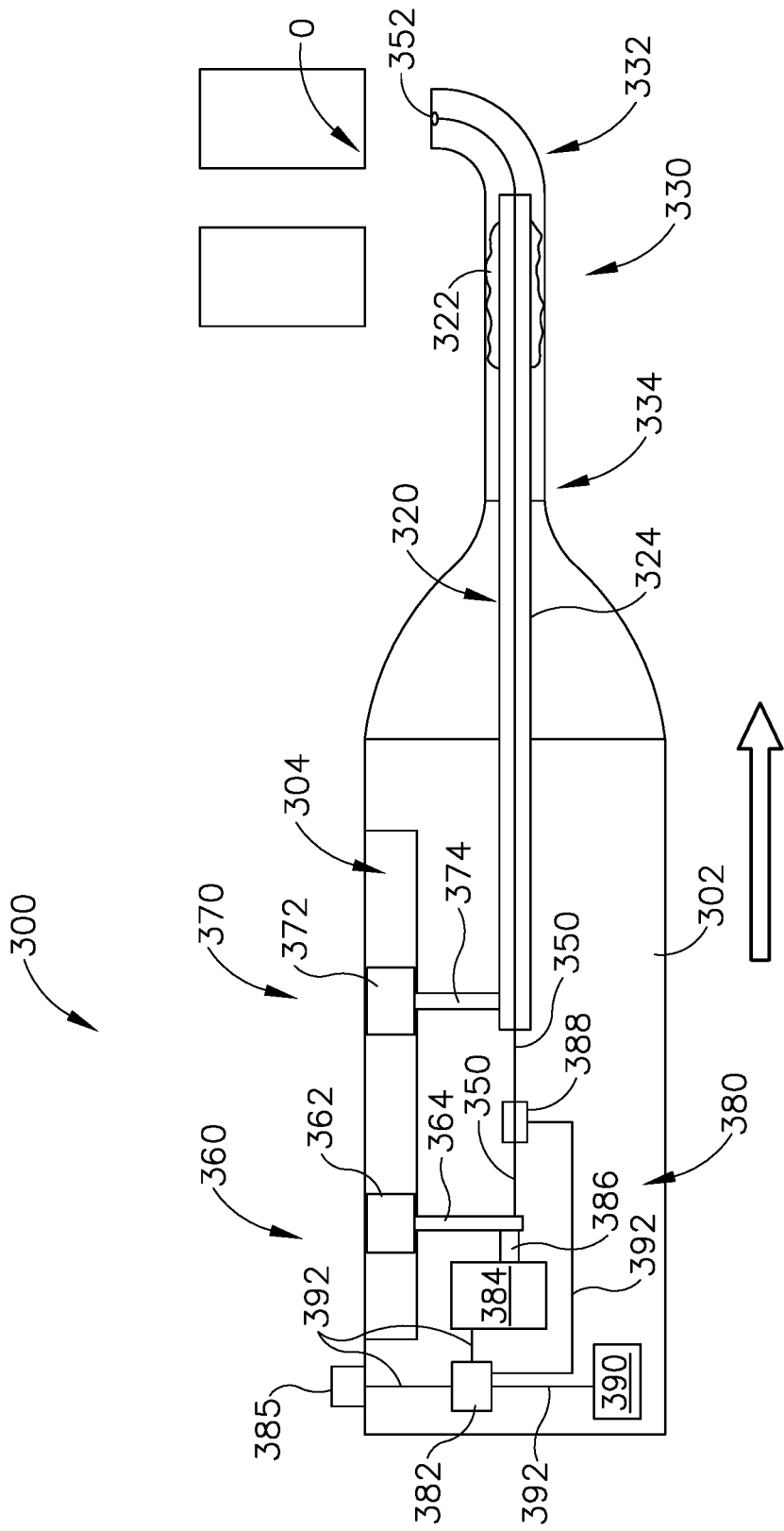
FIG. 7E depicts a side schematic view of the instrument of FIG. 7A, where the distal portion of the guide catheter of FIG. 7A is positioned distally in relation to a targeted ostium of a patient and the guidewire of FIG. 7A is within the guide catheter.

As shown in FIG. 7C, control module (382), having all the necessary parameters either entered or preloaded, activates actuation assembly (384), which in turn distally drives rod (386), guidewire movement mechanism (360), and guidewire (350) until distal tip (352) of guidewire (350) contacts an anatomical structure next to ostium (O). Force transducer (388) measures the forces created within guidewire (350) due to contact between the anatomical structure and distal tip (352) of guidewire (350), and sends a signal to control module (382) indicating distal tip (352) has hit an anatomical structure without entering ostium (O). As a result, as shown in FIG. 7D, control module (382) directs actuation assembly (382) to proximally retract guidewire movement mechanism (360) and guidewire (350) in order to start a new actuation cycle. At this point, control module (382) may automatically direct actuation assembly (384) to restart an actuation cycle, or may wait until a user confirms the start of a new actuation cycle via activation input (385). Either way, as shown in FIG. 7E, a user may move handle (302) in order to attempt to align the open distal end of bent distal portion (334) of guide catheter (330) with ostium (O). However, a user mistakenly moves handle (302) too far in this example, but the actuation cycle starts again.

Figure 7F:
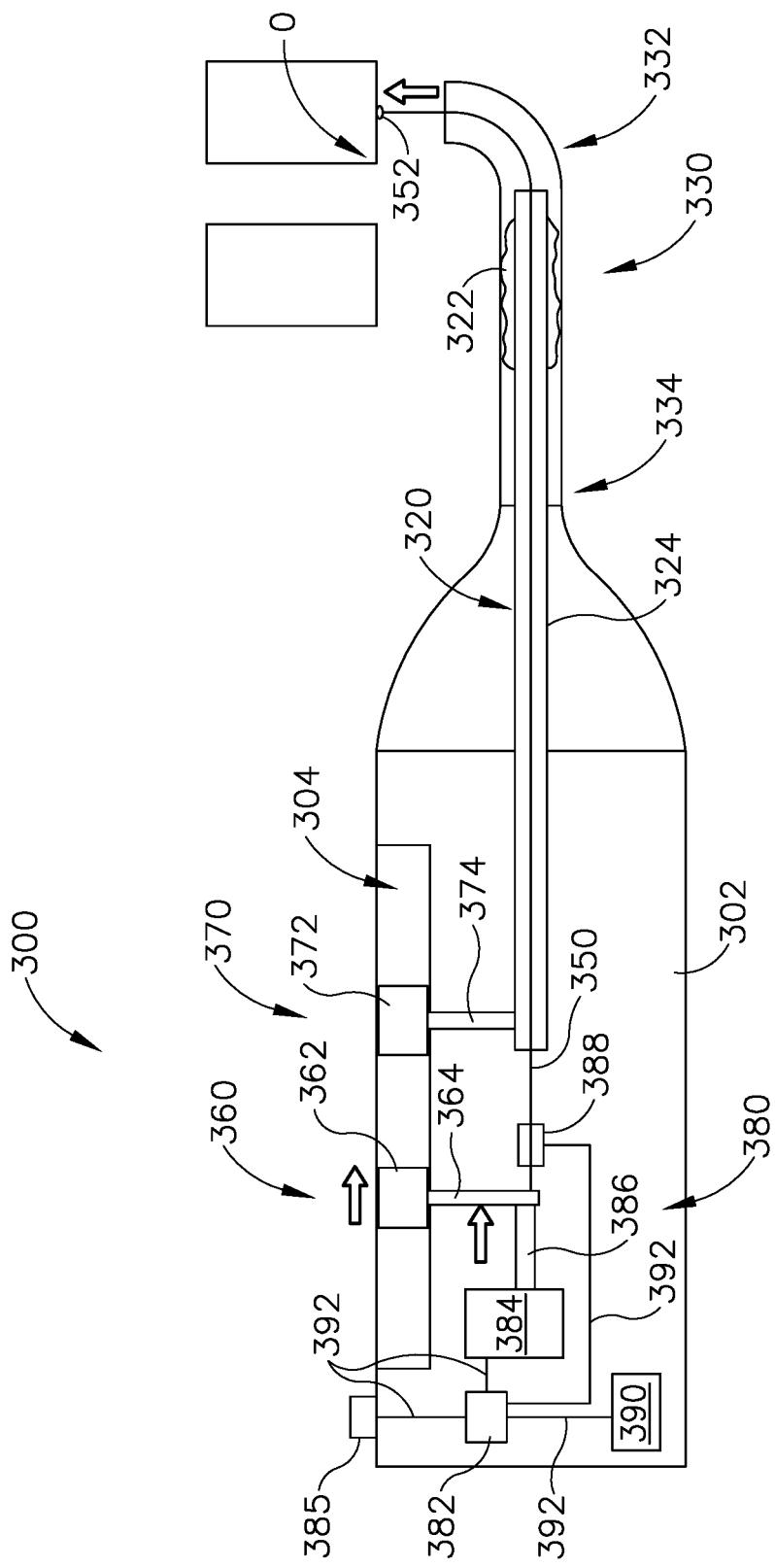
FIG. 7F depicts a side schematic view of the instrument of FIG. 7A, where the distal portion of the guide catheter of FIG. 7A is positioned distally in relation to a targeted ostium of a patient and the guidewire of FIG. 7A has exited the distal portion of the guide catheter.
Figure 7G:
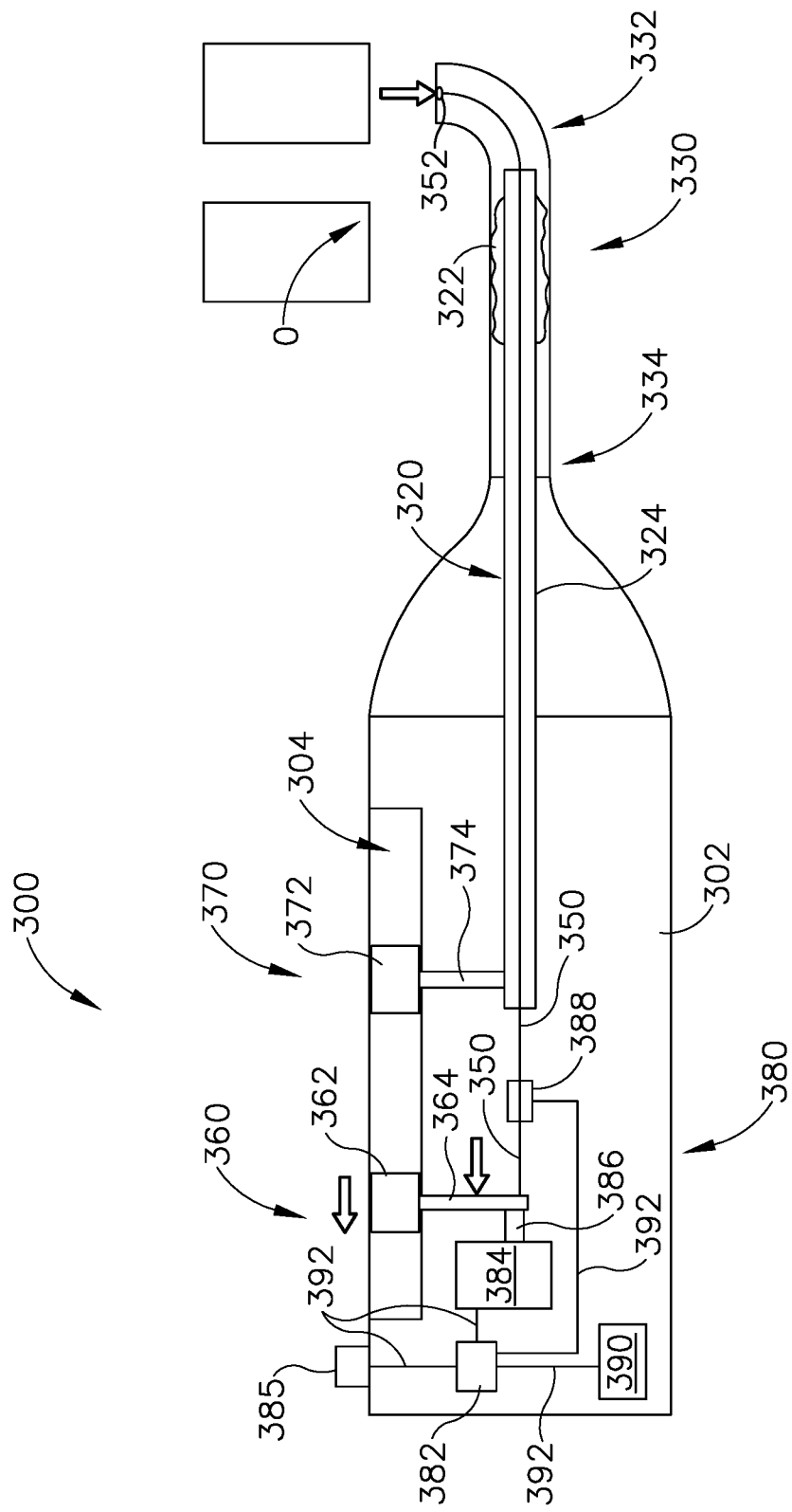
FIG. 7G depicts a side schematic view of the instrument of FIG. 7A, where the distal portion of the guide catheter of FIG. 7A is positioned distally in relation to a targeted ostium of a patient and the guidewire of FIG. 7A is within the guide catheter.
Figure 7H:
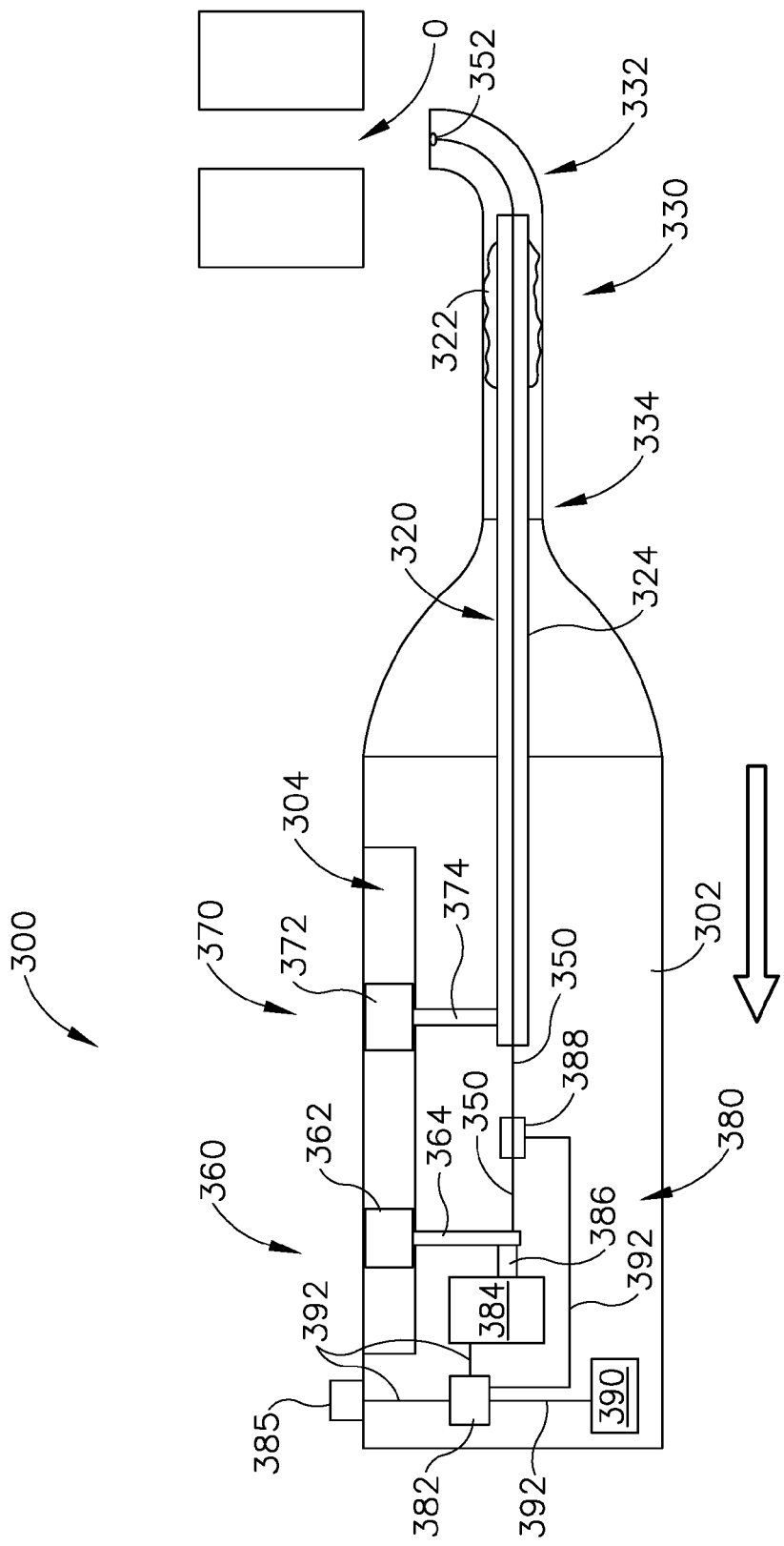
FIG. 7H depicts a side schematic view of the instrument of FIG. 7A, where the distal portion of the guide catheter of FIG. 7A is aligned in relation to a targeted ostium of a patient and the guidewire of FIG. 7A is within the guide catheter.
Figure 71:
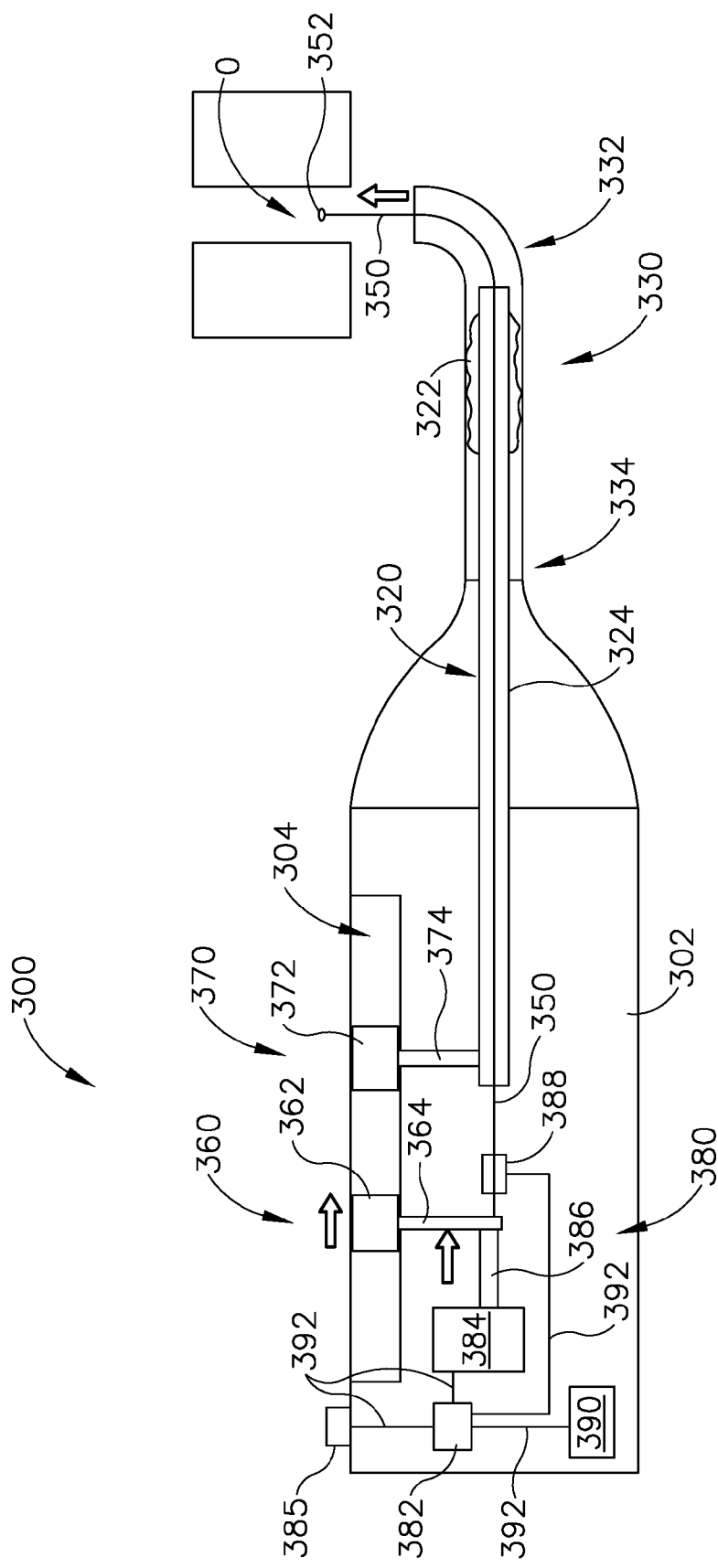

As shown in FIG. 7F, control module (382) reactivates actuation assembly (384) to start a new actuation cycle, which in turn distally drives rod (386), guidewire movement mechanism (360), and guidewire (350) until distal tip (352) of guidewire (350) contacts another anatomical structure that is next to ostium (O). Force transducer (388) measures the forces created within guidewire (350) due to contact between the anatomical structure and distal tip (352) of guidewire (350), and sends a signal to control module (382) indicating distal tip (352) has hit an anatomical structure of the patient without entering ostium (O). As a result, as shown in FIG. 7G, control module (382) directs actuation assembly (382) to proximally retract guidewire movement mechanism (360) and guidewire (350) in order to start a new actuation cycle. At this point, control module (382) may automatically direct actuation assembly (384) to restart an actuation cycle, or may wait until a user confirms the start of a new actuation cycle via activation input (385). Either way, as shown in FIG. 7H, a user may move handle (302) again in order to attempt to align the open distal end of bent distal portion (334) of guide catheter (330) with ostium (O). This time, a user properly aligns the open distal end of bent distal portion (332) with ostium (O).

As shown in FIG. 7I control module (382) reactivates actuation assembly (384) to start a new actuation cycle, which in turn distally drives rod (386), guidewire movement mechanism (360), and guidewire (350) until distal tip (352) of guidewire (350) has traveled the predetermined distance loaded onto control module (382). Actuation assembly (384) sends control module (382) a signal indicative that distal tip (352) of guidewire (350) has reached the predetermined distance without force transducer (388) signaling to control module (382) that distal tip (352) contacted an anatomical structure of a patient indicative of not entering ostium (O). As a result, control module (382) deactivates actuation assembly (384) as to not actuate guidewire (350) any more. At this point, control module (382) may signal to activation input (385) that distal tip (352) of guidewire (350) is within the desired ostium (O). Activation input (385) may indicate to a user that guidewire (350) is within ostium (O). By way of example only, activation input (385) may emit one or more audible sounds, provide visual feedback (e.g., flashing light), and/or give tactile feedback to indicate to a user guidewire (350) is properly placed.

Figure 7J:
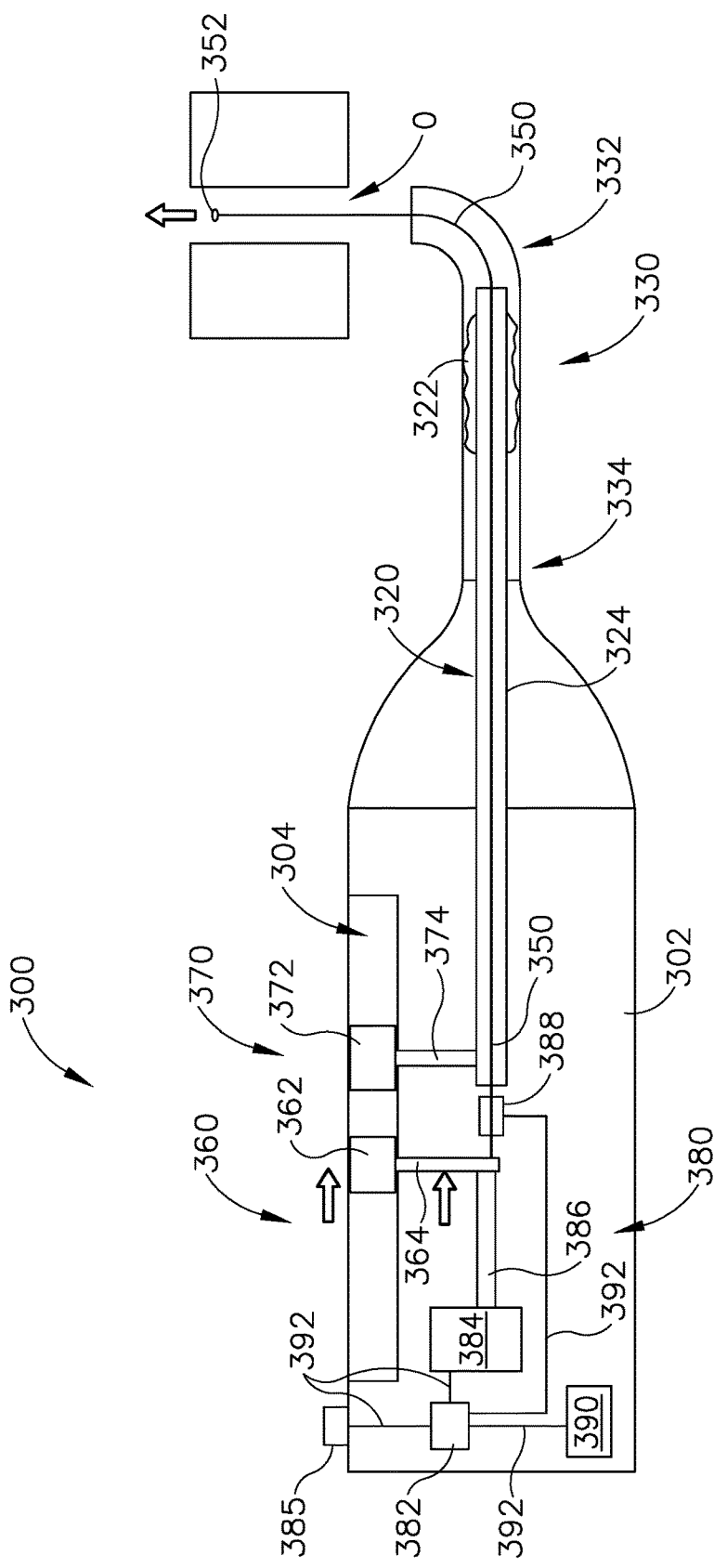
FIG. 7J depicts a side schematic view of the instrument of FIG. 7A, where the distal portion of the guide catheter of FIG. 7A is aligned in relation to a targeted ostium of a patient and the guidewire of FIG. 7A is further inserted through the ostium.
Figure 7K:
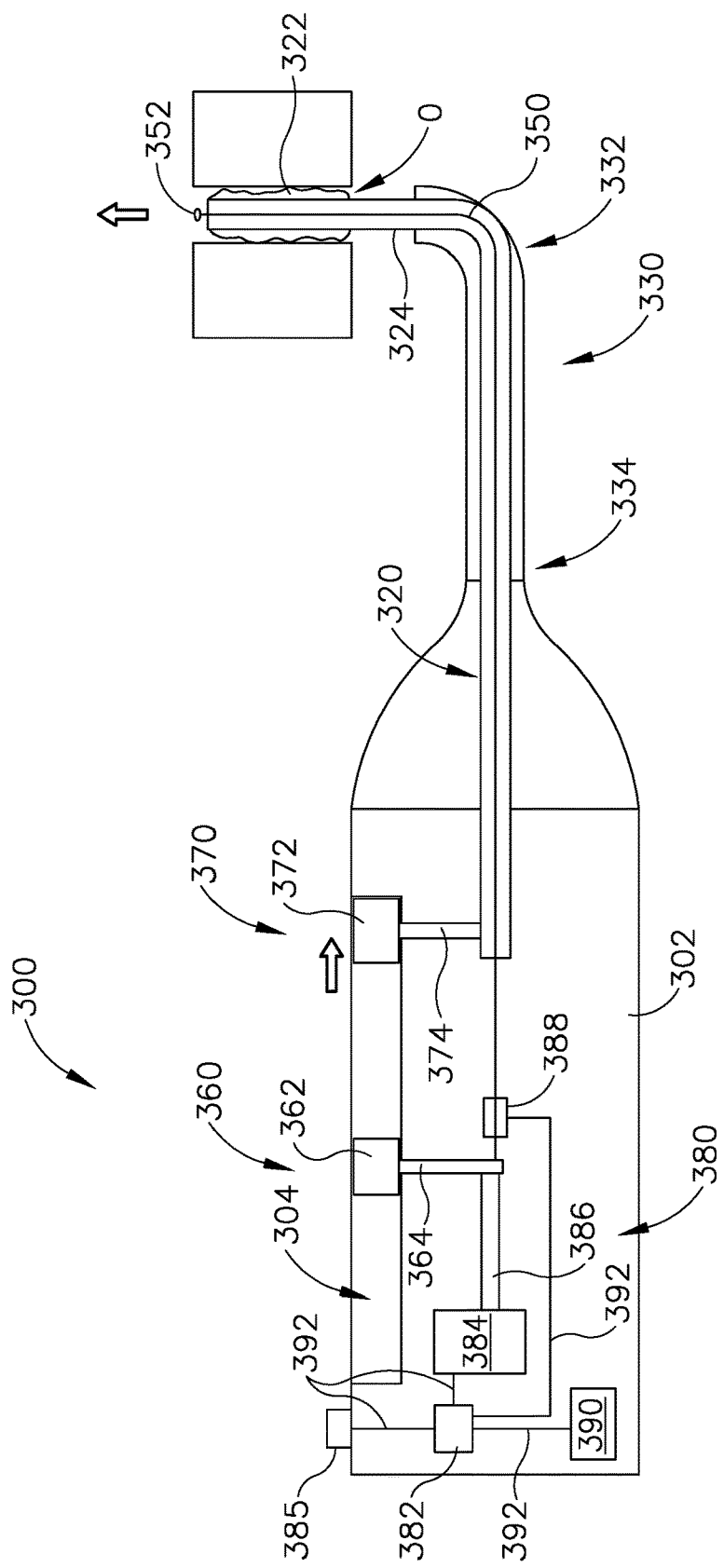
FIG. 7K depicts a side schematic view of the instrument of FIG. 7A, where the distal portion of the guide catheter of FIG. 7A is aligned in relation to a targeted ostium of a patient, the guidewire of FIG. 7A is through the ostium, and a guide catheter is advanced out the guide catheter and over the guidewire within the ostium.
Figure 7L:
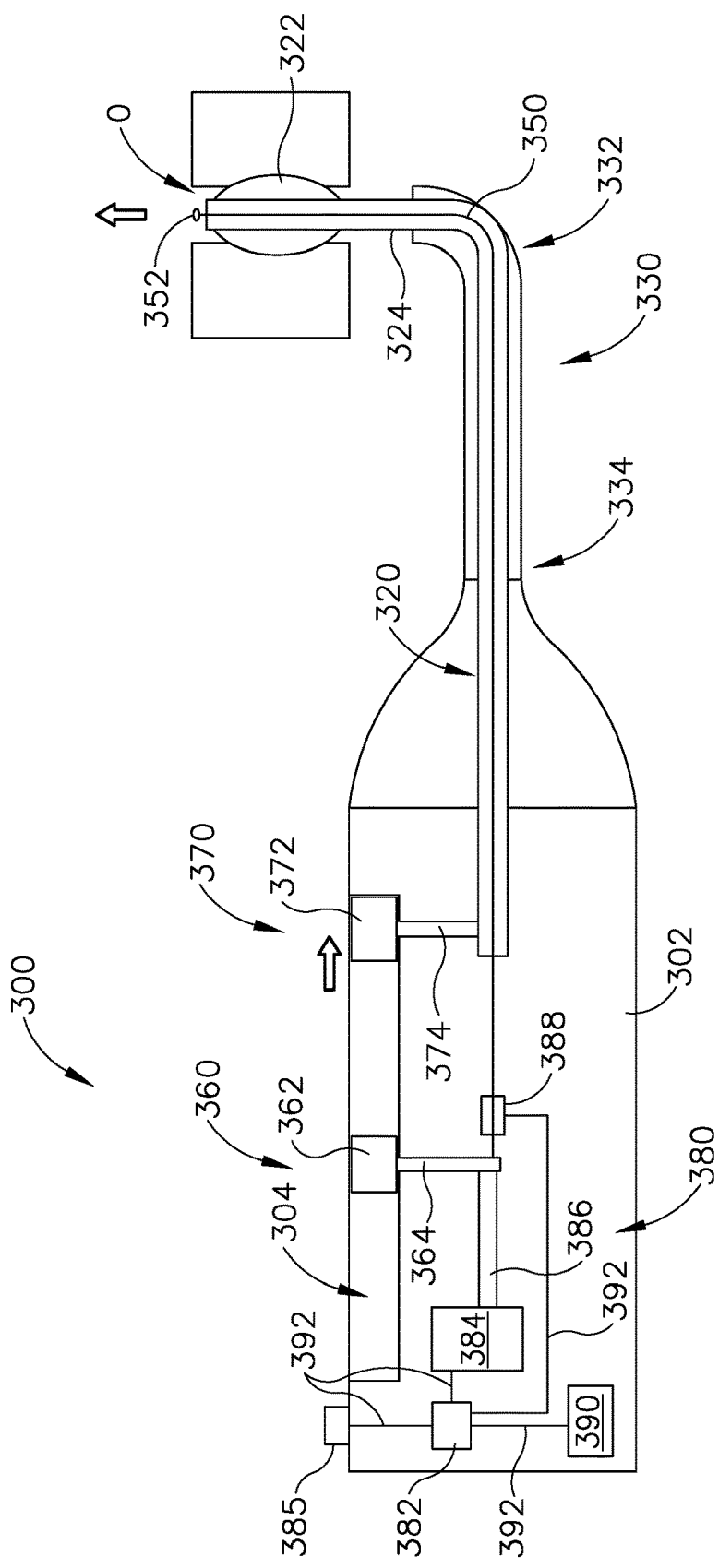
FIG. 7L depicts a side schematic view of the instrument of FIG. 7A, where the distal portion of the guide catheter of FIG. 7A is aligned in relation to a targeted ostium of a patient, the guidewire of FIG. 7A is through the ostium, and the guide catheter of FIG. 7K is advanced out the guide catheter and over the guidewire within the ostium, and a dilator is inflated.

At his point, as shown in FIG. 7J, a user may manually advance slide (362) in order to advance guidewire (350) further within ostium (O). Next, as shown in FIG. 7K, a user may actuate slide (372) in order to slide dilation catheter (320) along guidewire (350) such that dilator (322) is properly located. Next, as shown in FIG. 7L, a user may dilate dilator (322) in order to expand ostium (O). Dilation may occur through any means described above or through any other suitable means known to a person having ordinary skill in the art in view of the teachings herein.

V. Exemplary Dilation Catheter Instrument with Onboard Light

In some instances, it may be desirable to have an onboard light source that may connect with guidewire (50, 150, 250, 350) in order to provide for transillumination as described above. In instances where a light source is external to instrument (100, 200, 300), there may be a cord communicating light extending from light source to instrument (100, 200, 300). This cord may cause inconvenience by tangling or inadvertently being snagged. Therefore, adding an onboard light source may add to ease of use.

Figure 8:
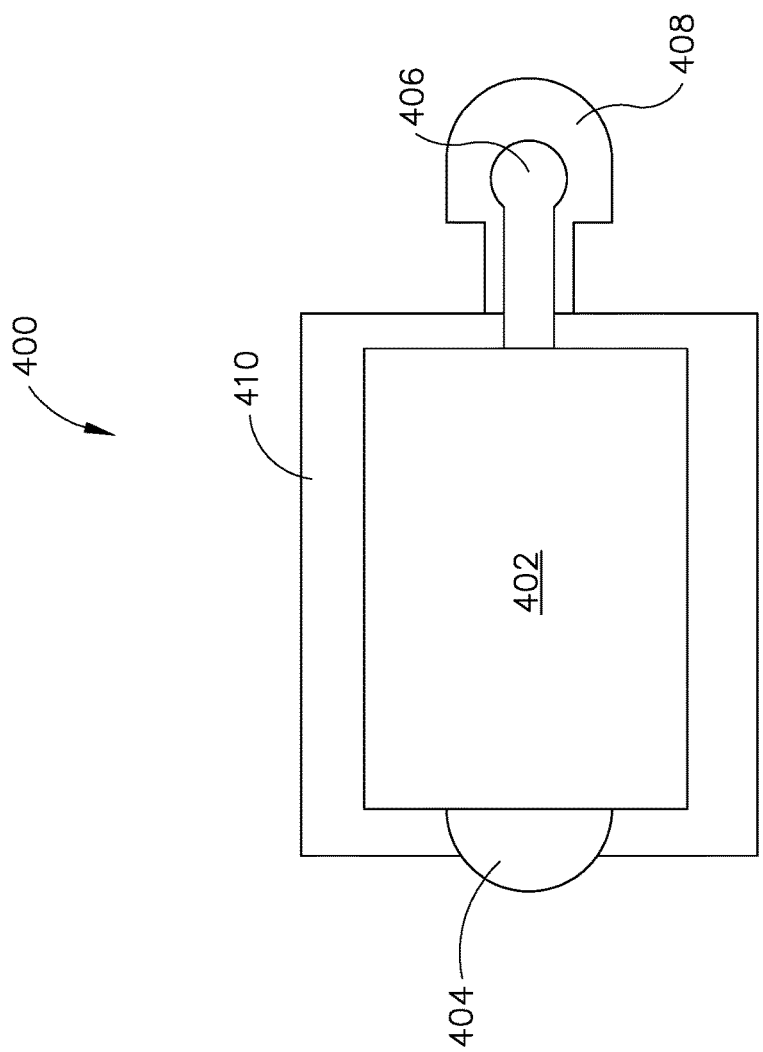
FIG. 8 depicts a side schematic view of a portable battery handle and light source that may be readily incorporated into the dilation catheter system of FIG. 1.
Figure 9:
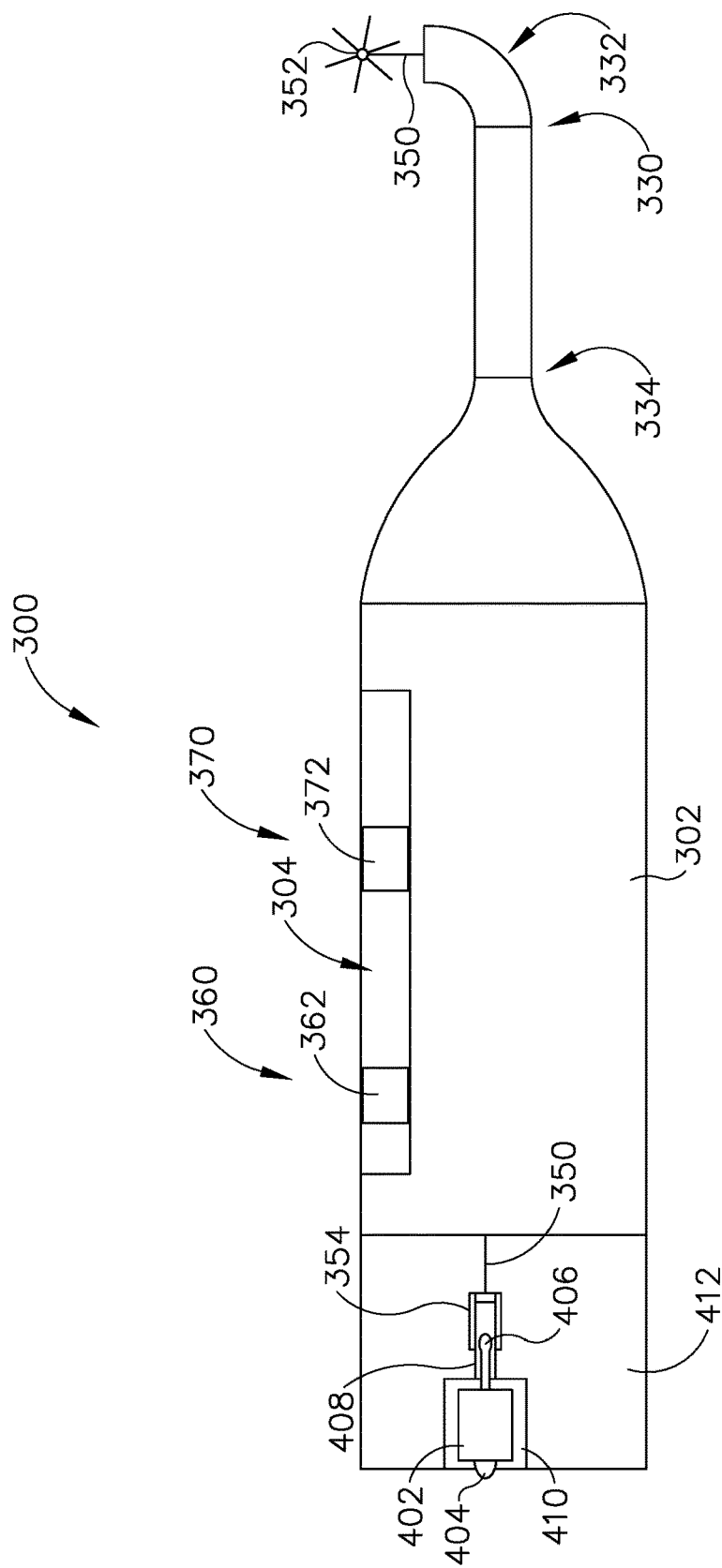
FIG. 9 depicts a side schematic view of the portable battery handle and light source of FIG. 8 coupled to the instrument of FIG. 7A.

FIGS. 8-9 show an exemplary onboard light source (400) that may be integrated into handle (102, 202, 302) described above. Onboard light source (400) includes a battery (402) housed within a cover (410), a button (404) configured to selectively activate battery (402), an LED (406) in communication with batter (402), and a luer fitting (408) configured to couple LED (406) with the proximal end of guidewire (50, 150, 250, 350). As shown in FIG. 9, luer fitting (408) may couple with guidewire (350), while cover (410) may affix onboard light source (400) with proximal end of handle (302). Button (404) may be pushed in order to activate LED (406) via battery (402). Therefore, onboard light source (400) may directly couple with handle (302) and also illuminate guidewire (350), eliminating the need to use an external light source.

Onboard light source (400) may also be configured and operable in accordance with at least some of the teachings of U.S. patent application Ser. No. 14/834,936, filed on Aug. 25, 2015, issued as U.S. Pat. No. 10,123,685 on Nov. 13, 2018, entitled "Apparatus and Method to Illuminate and Orient Guidewire," the disclosure of which is incorporated by reference herein.

VI. Exemplary Desktop Inflation and Illumination Kit

It may be desirable to include a desktop kit having both an illumination assembly (providing a light source for an illuminating guidewire, etc.) and an inflation assembly (providing pressurized fluid to inflate a dilator, etc.). Additionally, it may be desirable to have an inflation assembly that automatically primes a balloon catheter by removing air from an inflation line; and that also dials in the correct pressure for inflating a balloon dilator. This may eliminate the need for an assistant to prime a balloon catheter and dial in the correct pressure, which may otherwise create inconsistencies.

Figure 10:
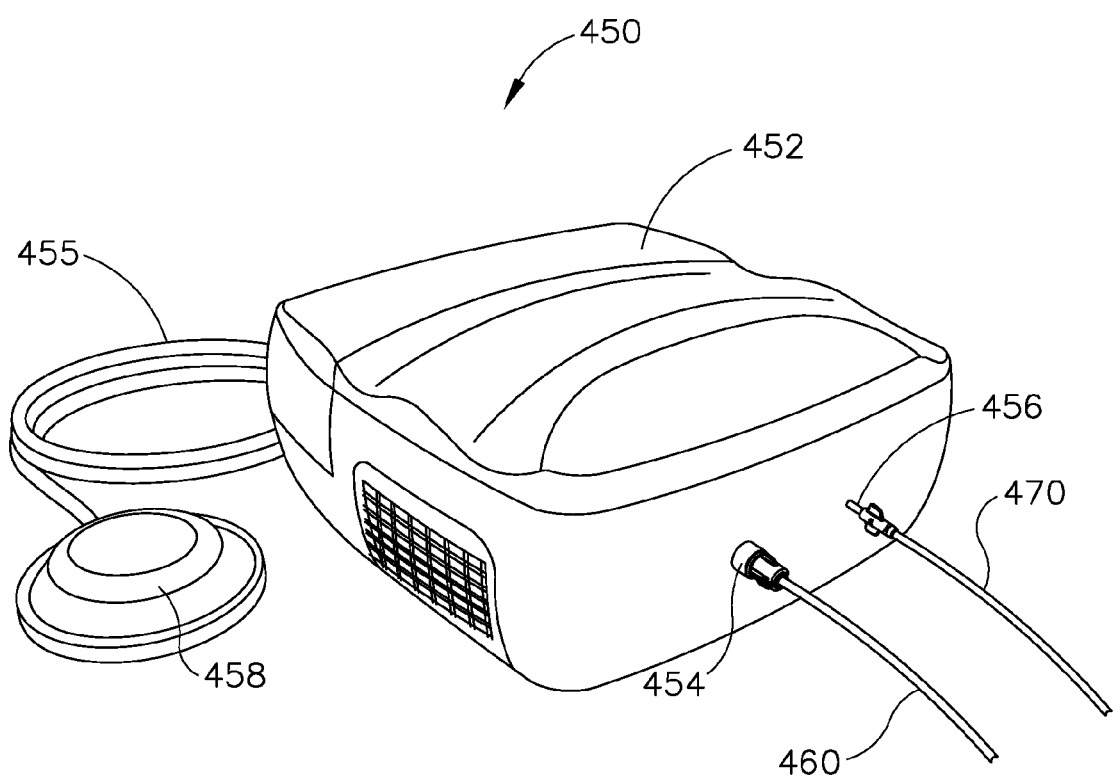
FIG. 10 depicts a perspective view of a desktop inflation and illumination kit that may be readily incorporated into the dilation catheter system of FIG. 1.
Figure 11:
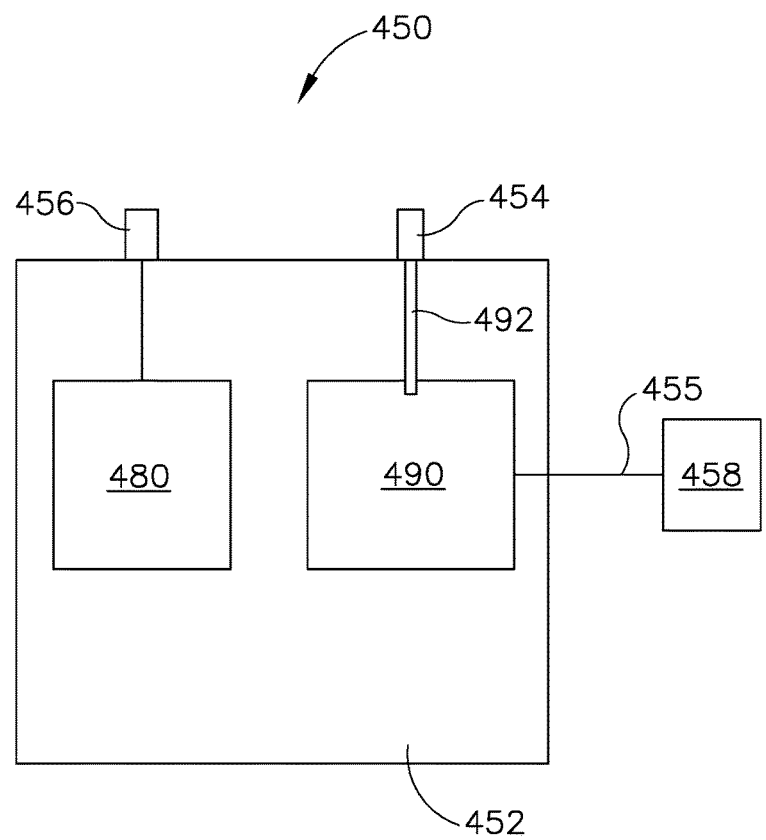
FIG. 11 depicts a schematic diagram of the desktop inflation and illumination kit of FIG. 10.

FIGS. 10-11 show an exemplary desktop inflation/illumination kit (450). Inflation/illumination kit includes a housing (452) storing an illumination assembly (480), a motorized inflation assembly (490), an illumination port (456) connected to illumination assembly (480), an inflation port (454) in fluid communication with motorized inflation assembly (490) via tube (492), a foot pedal (458) in electrical communication with motorized inflation assembly (490) via wire (455), an inflation lumen (460) connected to inflation port (454), and a light cable (470) connect to illumination port (456).

Illuminating assembly (480) is configured to generate a suitable light for the distal end of a guidewire, which may be communication through illumination port (456) and light cable (470). Illumination assembly (490) may be activated by a button on housing (452) or any other suitable activation apparatus that would be apparent to a person having ordinary skill in the art in view of the teachings herein.

Additionally, motorized inflation assembly (490) may pump inflation fluid to a balloon via inflation tube (492), inflation port (454), and inflation lumen (460). Motorized inflation assembly (490) may be activated to pump inflation fluid to/from a balloon by activation of foot pedal (458), which generates a signal to motorized inflation assembly (490) via wire (455). Motorized inflation assembly (490) may be capable of priming balloon, and controlling and regulating both pressure and inflation/deflation speed. Housing (452) may have externally visible lights and audible tones that communicate function of motorized inflation assembly (490) or illumination assembly (480).

Desktop inflation/illumination kit (450) may also be constructed and operable in accordance with at least some of the teachings of U.S. Pub. No. 2016/0058985, entitled "Automated Inflator for Balloon Dilator," published Mar. 3, 2016, now abandoned, disclosure of which is incorporated by reference herein.

VII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a handle; (b) a guide member extending distally from the handle; (c) a dilation catheter slidably housed within the handle, wherein the dilation catheter is slidable relative to the guide member; (d) a guidewire translatable relative to the dilation catheter; (e) a first movement assembly configured to actuate relative to the handle, wherein the first movement assembly comprises: (i) a first body fixed with the dilation catheter, and (ii) a first coupling member; and (f) a second movement assembly configured to actuate relative to the handle, wherein the second movement assembly is proximal in relation to the first movement assembly, wherein the second movement assembly comprises: (i) a second body configured to selectively fix to the guidewire, wherein the second body is configured to actuate relative to the handle, and (ii) a second coupling member associated with the second body, wherein the first coupling member and the second coupling member are configured to connect the first movement assembly and the second movement assembly to translate together relative to handle in response to distal translation of the first movement assembly.

Example 2

The apparatus of Example 1, further comprising a stop associated with the handle, wherein the stop is configured to disconnect the second movement assembly from the first movement assembly.

Example 3

The apparatus of Example 2, wherein the stop is configured to contact the second movement assembly to prevent further distal translation of the second movement assembly.

Example 4

The apparatus of Example 3, wherein the handle defines a first slot, wherein a portion of the second body is slidably disposed within the first slot, wherein the stop is located with the first slot.

Example 5

The apparatus of Example 4, wherein the handle defines a second slot, wherein the first body is slidably disposed within the second slot.

Example 6

The apparatus of any one or more of Examples 2 through 5, wherein the stop is selectively movable relative to the handle.

Example 7

The apparatus of any one or more of Examples 1 through 6, wherein the first movement assembly comprises a finger grip, wherein the finger grip is rotatably coupled with the first body, wherein the first coupling member is fixed to the finger grip.

Example 8

The apparatus of Example 7, wherein the first coupling member comprises a rotational transfer element, wherein the rotational transfer element is configured to convert rotation of the finger grip relative to the first body into rotation of the guidewire about a longitudinal axis defined by the guidewire.

Example 9

The apparatus of Example 8, wherein the finger grip defines a longitudinal pathway configured to receive the guidewire.

Example 10

The apparatus of any one or more of Examples 8 through 9, wherein the second body further comprises a slide member and a rotating member, wherein the rotating member is rotatably coupled to the slide member, wherein the slide member is configured to translate relative to the handle.

Example 11

The apparatus of Example 10, wherein the rotating member is configured to selectively fix to the guidewire.

Example 12

The apparatus of Example 11, wherein the second coupling member is fixed to the rotating member.

Example 13

The apparatus of Example 12, wherein the rotating member comprises a rotational bearing.

Example 14

The apparatus of claim 12, wherein the rotational transfer member comprises a plurality of teeth.

Example 15

The apparatus of any one or more of Examples 1 through 14, wherein the first coupling member and the second coupling member comprise a magnet.

Example 16

The apparatus of any one or more of Examples 1 through 15, wherein the first coupling member and the second coupling member comprise a snap-fit feature.

Example 17

An apparatus comprising: (a) a handle; (b) a guide member extending distally from the handle; (c) a dilation catheter slidably housed within the handle, wherein the dilation catheter is slidable relative to the guide member; (d) a guidewire translatable relative to the dilation catheter, wherein the guidewire comprises a distal tip; (e) a first movement assembly configured to actuate relative to the handle, wherein the first movement assembly is fixed to the dilation catheter; (f) a second movement assembly configured to actuate relative to the handle, wherein the second movement assembly is configured to selectively fix to the guidewire; and (g) a guidewire placement assembly configured to actuate the second movement assembly distally to a predetermined distance, wherein the guidewire placement assembly is configured to detect forces acting on the distal tip of the guidewire, wherein the guidewire placement assembly is configured to actuate the second movement assembly proximally if the detected force exceeds a predetermined force threshold before the second movement assembly actuates the predetermined distance.

Example 18

The apparatus of Example 17, wherein the guidewire placement assembly comprises a control module configured to compare forces acting on the distal tip of the guidewire with the predetermined force threshold, wherein the control module is configured to compare the predetermined distance with an actual distance of the second movement assembly.

Example 19

The apparatus of any one or more of Examples 17 through 18, wherein the guidewire placement assembly comprises a force transducer associated with the guidewire.

Example 20

An apparatus comprising: (a) a handle; (b) a guide member extending distally from the handle; (c) a dilation catheter slidably housed within the handle, wherein the dilation catheter is slidable relative to the guide member; (d) a guidewire translatable relative to the dilation catheter, wherein the guidewire comprises a distal tip; (e) a first movement assembly configured to actuate relative to the handle, wherein the first movement assembly is fixed to the dilation catheter; (f) a second movement assembly configured to actuate relative to the handle, wherein the second movement assembly is configured to selectively fix to the guidewire; and (g) an onboard light source configured to couple with the handle, wherein the onboard light source is further configured to couple with a proximal end of the guidewire.

VIII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, examples, etc. described herein may be combined with any one or more of the other teachings, expressions, examples, examples, etc. that are described herein. The above-described teachings, expressions, examples, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, examples, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
   (a) a handle;
   (b) a guide member extending distally from the handle;
   (c) a dilation catheter slidably housed within the handle, wherein the dilation catheter is slidable relative to the guide member;
   (d) a guidewire translatable relative to the dilation catheter;
   (e) a first movement assembly configured to actuate relative to the handle, wherein the first movement assembly comprises:
      (i) a first body fixed with the dilation catheter, and
      (ii) a first coupling member; and
   (f) a second movement assembly configured to actuate relative to the handle, wherein the second movement assembly is proximal in relation to the first movement assembly, wherein the second movement assembly comprises:
      (i) a second body configured to selectively fix to the guidewire, wherein the second body is configured to actuate relative to the handle, and
      (ii) a second coupling member associated with the second body, wherein the first coupling member and the second coupling member are configured to directly couple to fixedly connect the first movement assembly and the second movement assembly, wherein the first movement assembly and the second movement assembly when fixedly connected are configured to translate unitarily together relative to the handle in response to distal translation of the first movement assembly.

2. The apparatus of claim 1, further comprising a stop associated with the handle, wherein the stop is configured to disconnect the second movement assembly from the first movement assembly.

3. The apparatus of claim 2, wherein the stop is configured to contact the second movement assembly to prevent further distal translation of the second movement assembly.

4. The apparatus of claim 3, wherein the handle defines a first slot, wherein a portion of the second body is slidably disposed within the first slot, wherein the stop is located with the first slot.

5. The apparatus of claim 4, wherein the handle defines a second slot, wherein the first body is slidably disposed within the second slot.

6. The apparatus of claim 2, wherein the stop is selectively movable relative to the handle.

7. The apparatus of claim 1, wherein the first movement assembly comprises a finger grip, wherein the finger grip is rotatably coupled with the first body, wherein the first coupling member is fixed to the finger grip.

8. The apparatus of claim 7, wherein the first coupling member comprises a rotational transfer element, wherein the rotational transfer element is configured to convert rotation of the finger grip relative to the first body into rotation of the guidewire about a longitudinal axis defined by the guidewire.

9. The apparatus of claim 8, wherein the finger grip defines a longitudinal pathway configured to receive the guidewire.

10. The apparatus of claim 8, wherein the second body further comprises a slide member and a rotating member, wherein the rotating member is rotatably coupled to the slide member, wherein the slide member is configured to translate relative to the handle.

11. The apparatus of claim 10, wherein the rotating member is configured to selectively fix to the guidewire.

12. The apparatus of claim 11, wherein the second coupling member is fixed to the rotating member.

13. The apparatus of claim 12, wherein the rotating member comprises a rotational bearing.

14. The apparatus of claim 12, wherein the rotational transfer member comprises a plurality of teeth.

15. The apparatus of claim 1, wherein the first coupling member and the second coupling member comprise a snap-fit feature.

16. An apparatus comprising:
(a) a handle;
(b) a guide member extending distally from the handle;
(c) a dilation catheter slidably housed within the handle, wherein the dilation catheter is slidable relative to the guide member;
(d) a guidewire translatable relative to the dilation catheter, wherein the guidewire comprises a distal tip;
(e) a first movement assembly configured to actuate relative to the handle, wherein the first movement assembly is fixed to the dilation catheter;
(f) a second movement assembly configured to actuate relative to the handle, wherein the second movement assembly is configured to selectively fix to the guidewire; and
(g) a guidewire placement assembly configured to actuate the second movement assembly distally to a predetermined distance, wherein the guidewire placement assembly is configured to detect forces acting on the distal tip of the guidewire, wherein the guidewire placement assembly is configured to actuate the second movement assembly proximally if the detected force exceeds a predetermined force threshold before the second movement assembly actuates the predetermined distance, wherein the guidewire placement assembly is configured to prevent distal actuation of the second movement assembly if the detected force exceeds a predetermined force threshold before the second movement assembly actuates the predetermined distance.

17. The apparatus of claim 16, wherein the guidewire placement assembly comprises a control module configured to compare forces acting on the distal tip of the guidewire with the predetermined force threshold, wherein the control module is configured to compare the predetermined distance with an actual distance of the second movement assembly.

18. The apparatus of claim 16, wherein the guidewire placement assembly comprises a force transducer associated with the guidewire.

19. An apparatus comprising:
(a) a handle;
(b) a guide member extending distally from the handle;
(c) a dilation catheter slidably housed within the handle, wherein the dilation catheter is slidable relative to the guide member;
(d) a guidewire translatable relative to the dilation catheter;
(e) a first movement assembly configured to actuate relative to the handle, wherein the first movement assembly comprises:
(i) a first body fixed with the dilation catheter, and
(ii) a first coupling member; and
(f) a second movement assembly configured to actuate relative to the handle, wherein the second movement assembly is proximal in relation to the first movement assembly, wherein the second movement assembly comprises:
(i) a second body configured to selectively fix to the guidewire, wherein the second body is configured to actuate relative to the handle, and
(ii) a second coupling member associated with the second body, wherein the first coupling member and the second coupling member are configured to directly couple to fixedly connect the first movement assembly and the second movement assembly, wherein the first coupling member and the second coupling member comprise a magnet.

20. The apparatus of claim 1, further comprising an onboard light source configured to couple with the handle, wherein the onboard light source is further configured to couple with a proximal end of the guidewire.

* * * * *